United States Patent
Fujita et al.

(10) Patent No.: US 7,496,457 B2
(45) Date of Patent: Feb. 24, 2009

(54) LOAD BODY STATE JUDGING DEVICE, VEHICLE SEAT AND COMPUTER PROGRAM

(75) Inventors: Etsunori Fujita, Hiroshima (JP); Masato Enokizono, Oita (JP)

(73) Assignee: Delta Tooling Co., Ltd., Hiroshima (JP)

( * ) Notice: Subject to any disclaimer, the term of this patent is extended or adjusted under 35 U.S.C. 154(b) by 0 days.

(21) Appl. No.: 10/598,956

(22) PCT Filed: Mar. 22, 2005

(86) PCT No.: PCT/JP2005/005147

§ 371 (c)(1), (2), (4) Date: May 21, 2007

(87) PCT Pub. No.: WO2005/092193

PCT Pub. Date: Jun. 10, 2005

(65) Prior Publication Data

US 2007/0299636 A1    Dec. 27, 2007

(30) Foreign Application Priority Data

Mar. 25, 2004    (JP) ............................. 2004-089263

(51) Int. Cl.
*B60R 22/00* (2006.01)
*G06F 7/00* (2006.01)
*G06F 17/00* (2006.01)
(52) U.S. Cl. ................. 702/56; 297/216.15; 340/573.1; 340/576; 340/667; 701/45
(58) Field of Classification Search ............ 297/216.15; 340/573.1, 576, 667; 702/56
See application file for complete search history.

(56) References Cited

U.S. PATENT DOCUMENTS

| 5,498,028 | A | * | 3/1996 | Carlin et al. ................. 280/735 |
| 5,813,989 | A | * | 9/1998 | Saitoh et al. ................. 600/484 |
| 6,070,115 | A | * | 5/2000 | Oestreicher et al. ........... 701/45 |
| 6,195,008 | B1 | * | 2/2001 | Bader ...................... 340/573.1 |
| 6,337,629 | B1 | * | 1/2002 | Bader ........................ 340/576 |
| 6,392,550 | B1 | * | 5/2002 | Najor ........................ 340/576 |

FOREIGN PATENT DOCUMENTS

| JP | 6-197890 A | 7/1994 |
| JP | 9-308614 A | 12/1997 |
| JP | 10-076012 A | 3/1998 |
| JP | 10-146321 A | 6/1998 |
| JP | 2002-206594 A | 7/2002 |
| JP | 2002-336076 A | 11/2002 |
| JP | 2003-139192 A | 5/2003 |
| JP | 2004-344612 A | 12/2004 |
| JP | 2004-344613 A | 12/2004 |

* cited by examiner

*Primary Examiner*—Eliseo Ramos Feliciano
*Assistant Examiner*—Janet L Suglo
(74) *Attorney, Agent, or Firm*—WolfBlock LLP

(57) ABSTRACT

A load body state is judged from time series data of an emphasis displacement inclination obtained by collecting displacement signal data of the load body state using a displacement signal collection sensor, determining a rate of change for every arbitrary interval of an original waveform as an original waveform displacement inclination at an operating unit, and at the same time, determining time series data of an average displacement inclination for every prescribed time period range from a plurality of original waveform displacement inclinations, and by determining an emphasis displacement inclination through slide calculation of time series data of the average displacement inclination for every prescribed sampling time.

27 Claims, 30 Drawing Sheets

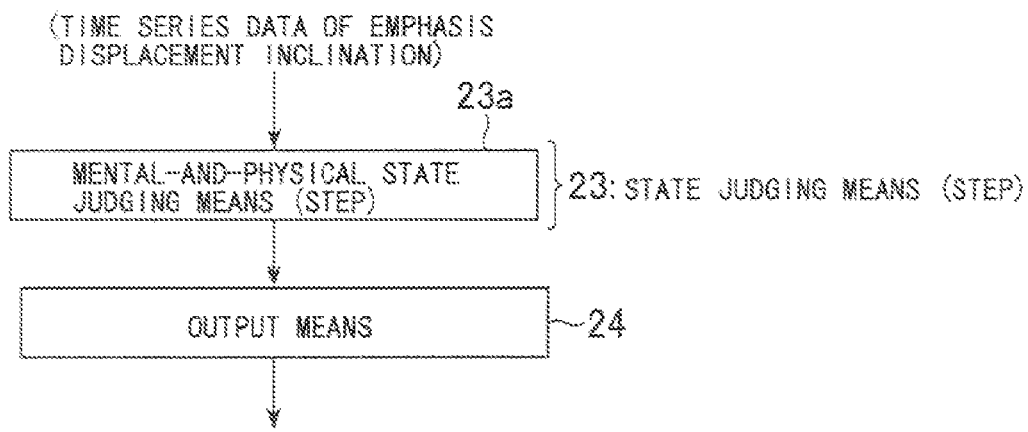
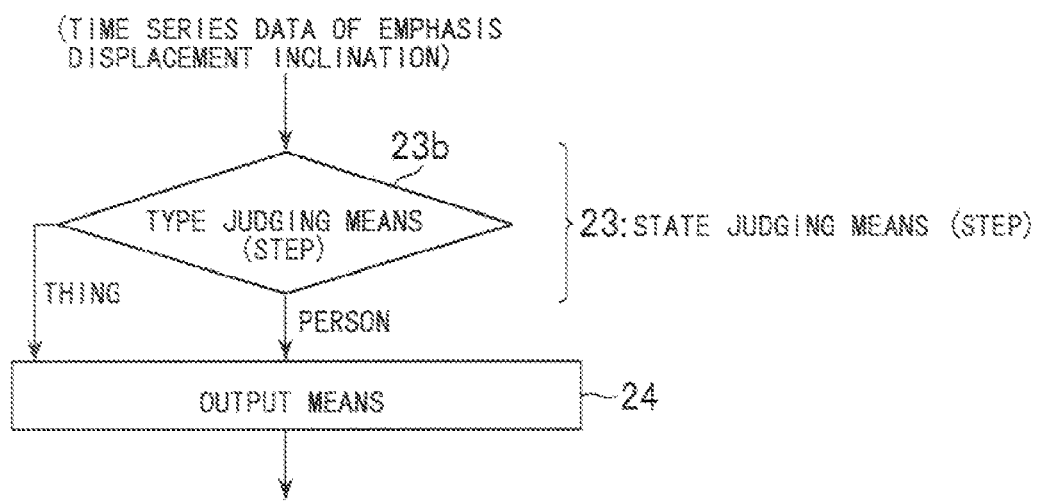
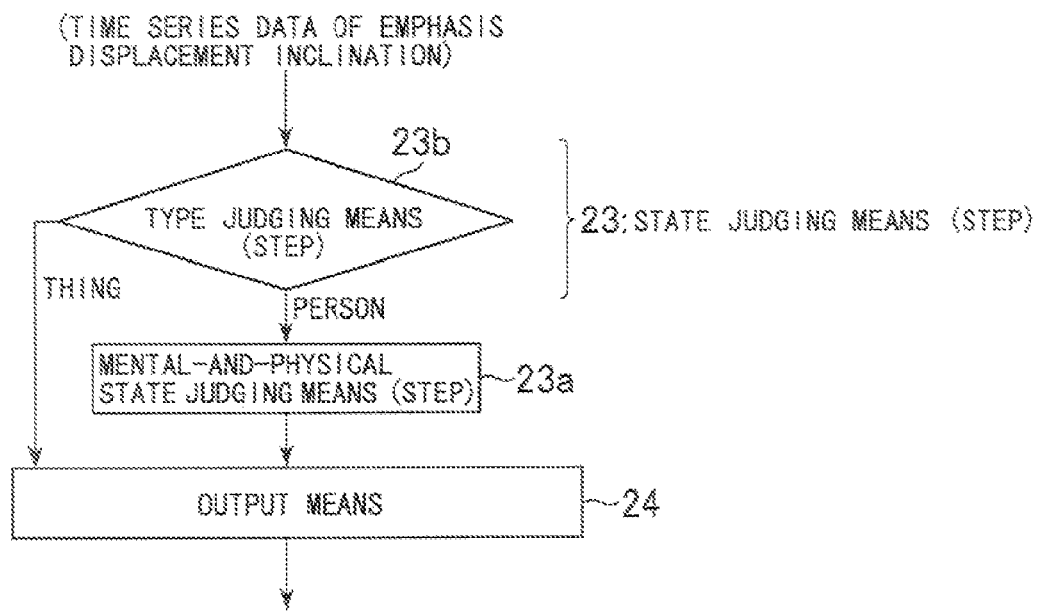

SLIDE CALCULATION LAP RATE = 90%

- ● – EMPHASIS DISPLACEMENT INCLINATION
- ○ – INCLINATION OF MAXIMUM LYAPUNOV INDEX a: HYPNAGOGIC OMEN SIGNAL
b: SIGNAL IN TRANSITION STATE INTO SLEEP
c: SLEEP SIGNAL

INCLINATION CALCULATION TIME = 180 s

— ● — EMPHASIS DISPLACEMENT INCLINATION
— ○ — INCLINATION OF MAXIMUM LYAPUNOV INDEX a: HYPNAGOGIC OMEN SIGNAL
b: SIGNAL IN TRANSITION STATE INTO SLEEP
c: SLEEP SIGNAL

IN THE CASE OF LAP RATE 90%

IN THE CAE OF SAMPLING TIME 180 SECONDS

IN THE CASE OF LAP RATE 90%

IN THE CAE OF SAMPLING TIME 180 SECONDS

COMPARISON OF 30 MINUTE SEATING EXPERIMENT
(TIME SERIES OF EMPHASIS DISPLACEMENT INCLINATION)

COMPARISON OF FREQUENCY ANALYSIS
(EMPHASIS DISPLACEMENT INCLINATION)
30 MINUTE SEATING EXPERIMENT

PULSE WAVE ORIGINAL WAVEFORM

F I G. 29
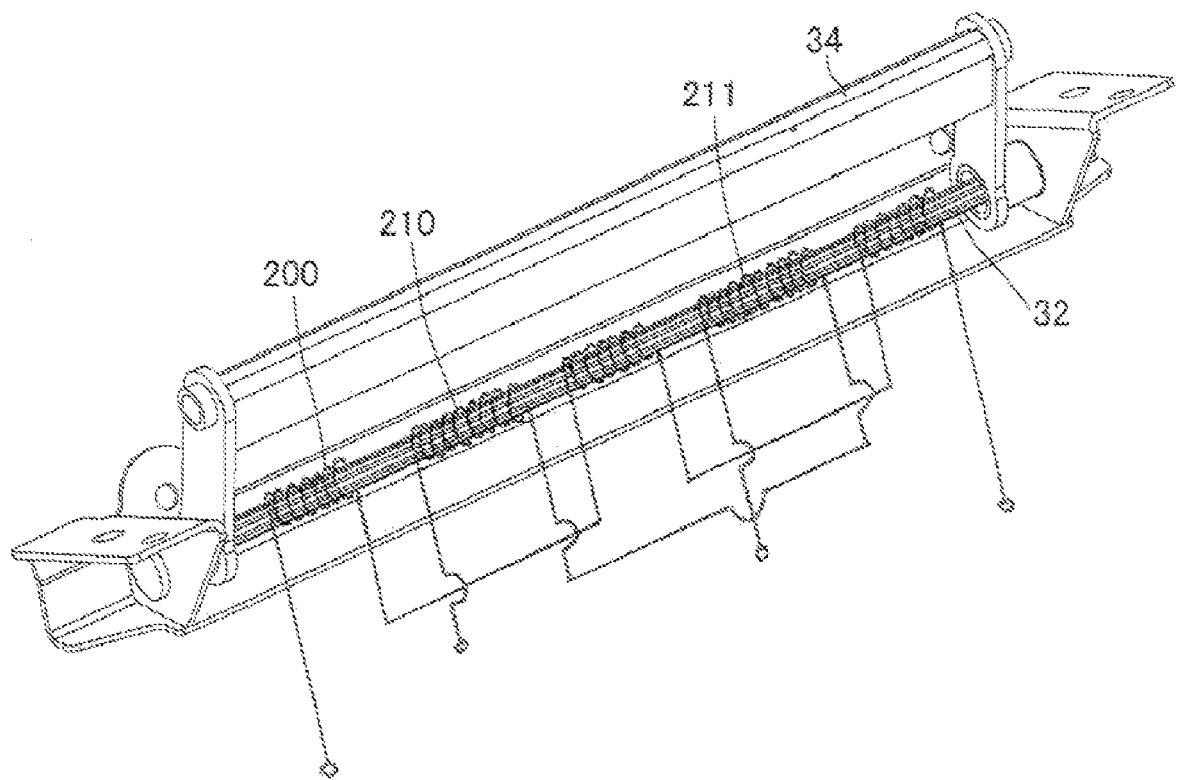

SAMPLING TIME: 10μs
EXCITING FREQUENCY: 50Hz

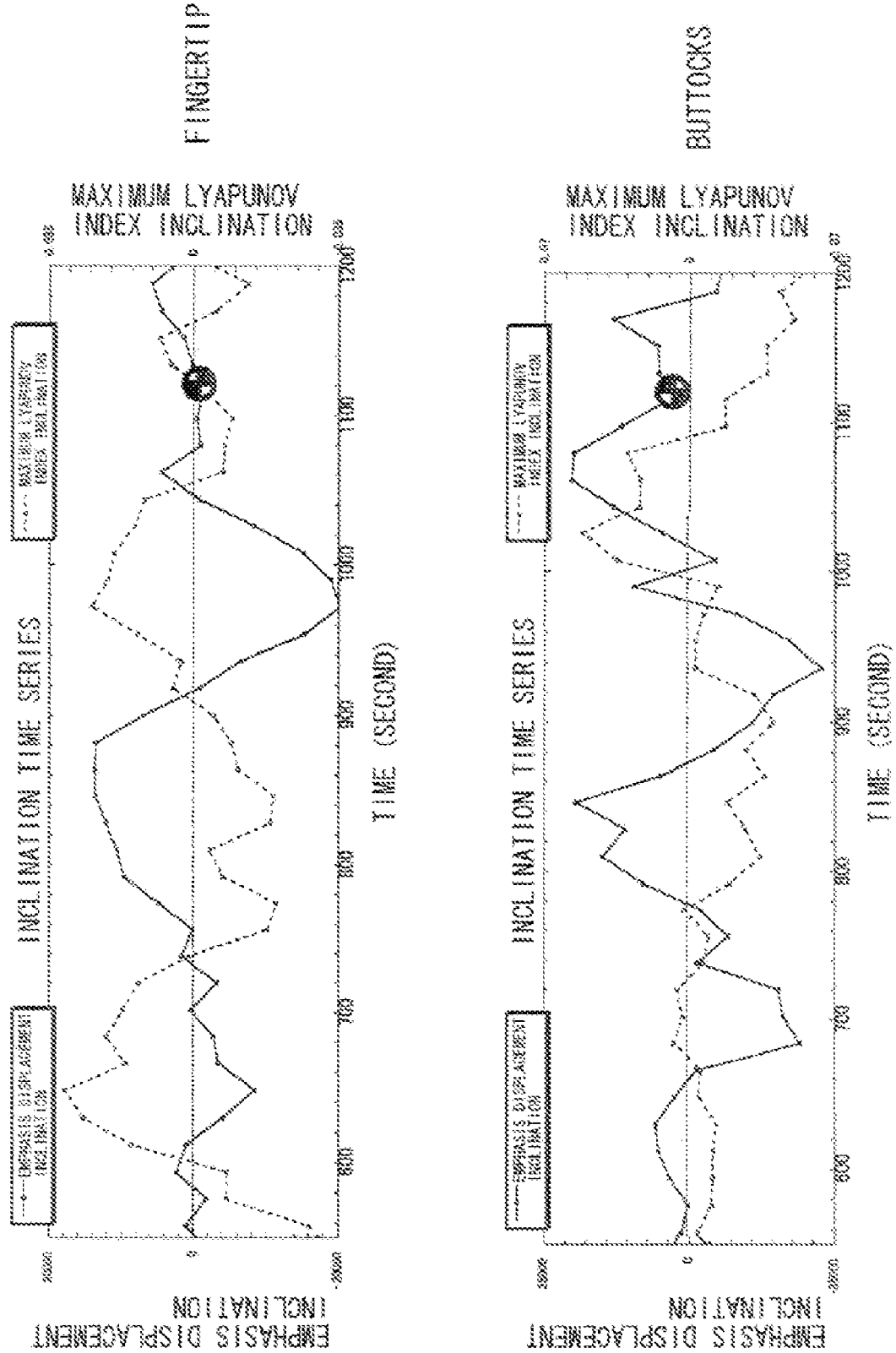

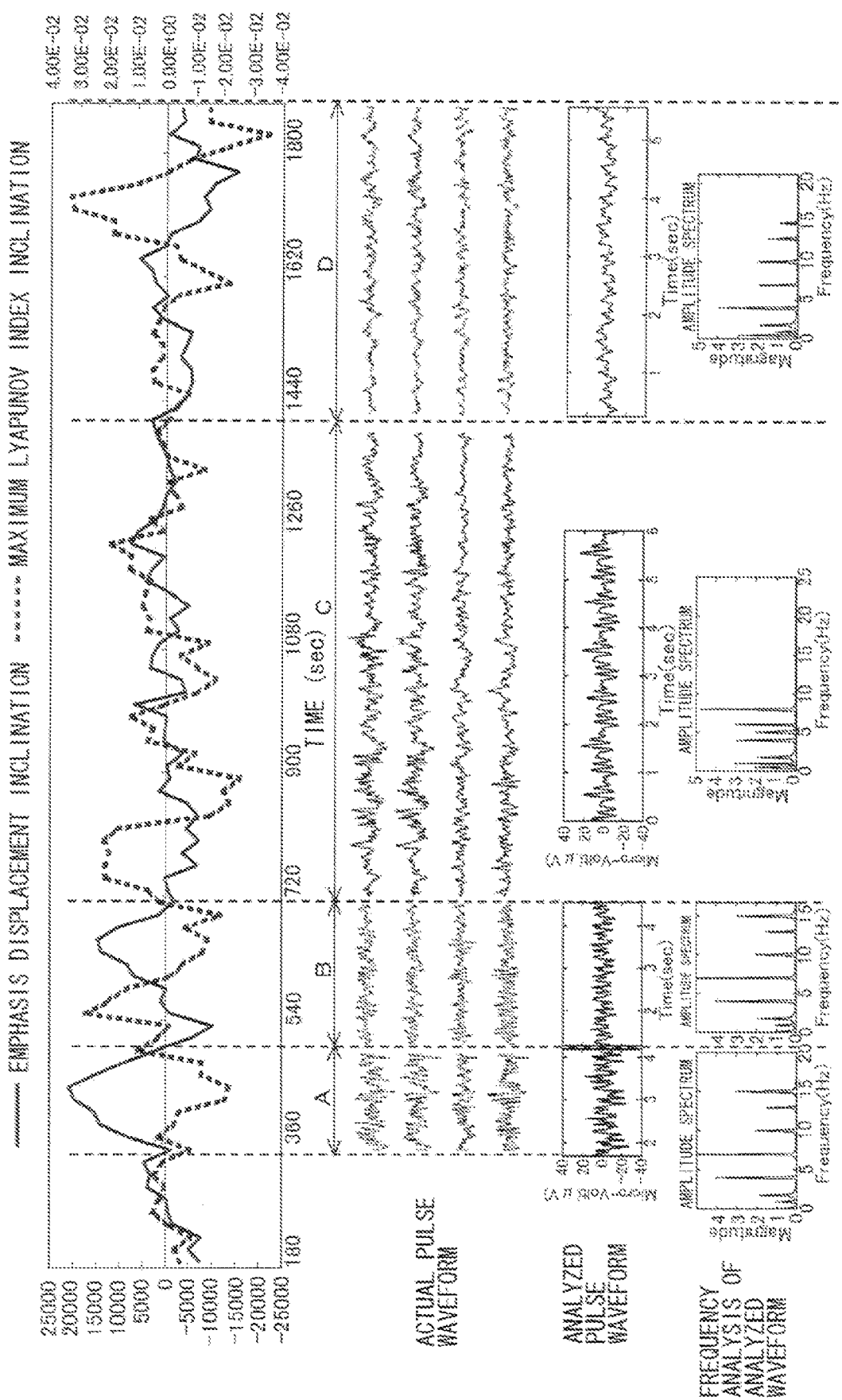

LOAD BODY STATE JUDGING DEVICE, VEHICLE SEAT AND COMPUTER PROGRAM

TECHNICAL FIELD

The present invention relates to a load body state judging device, provided to a load body supporting means originally used to support a person such as various seat, for instance, a vehicle seat used for a transportation devices such as cars, trains or air planes; an office-use seat; or a seat to be seated for a physical checkup, diagnosis or the like in a hospital or the like; or bedclothes such as bedding, a mattress, or a bed, and is able to automatically judge a load body state actually supported by the load body supporting means, and is especially suitable for judging a state of a load body supported by a vehicle seat; a vehicle seat provided with the load body type determining device; and a computer program used for load body state judgment.

BACKGROUND ART

In order to detect a living body state of a person, for instance, whether or not it is in an activated state (awakening state) or in a sleeping state, measurement of a brain wave and analysis of the brain wave pattern have been conventionally carried out. However, the measurement of a brain wave must be conducted under circumstances to restrict a human ordinary behavior such as necessity of setting a brain wave electrode or an ocular potential electrode on the head of a testee, and it is difficult to evaluate a living body state in a highly scientific level at the time of driving various transportation devices such as a car, a train or the like for instance without imposing a burden on the driver.

Whereas, monitoring a living body state (mental-and-physical state) of a driver while driving has been attracted recently as a countermeasure to prevent accident, and, for instance, a technology to use a heartbeat or a pulse beat for chaos analyzing it to monitor a living body state in Patent Document 1 and Patent Document 2. According to the technologies disclosed in Patent Documents 1 and 2, it is possible to evaluate a living body state of a driver easily without setting a large-scale device for brain wave measurement on the head.

Patent Document 1: Japanese Patent Application Laid-open No. Hei 9-308614

Patent Document 2: Japanese Patent Application Laid-open No. Hei 10-146321

DISCLOSURE OF THE INVENTION

Problem(s) to be Solved by the Invention

The devices disclosed in Patent Documents 1 and 2 are both for sensing vibration of a body surface accompanying a heartbeat by a pressure sensor mounted on a seat cushion of a seat. However, it is practically quite difficult to detect only vibration of the body surface accompanying the heartbeat of a seated person by the pressure sensor. In other words, when vibration of a body surface accompanying the heartbeat is tried to detect with such a pressure sensor, the pressure sensor sharply detects pressure changes due to vibration of a vehicle body. Therefore, it is difficult to clearly distinguish between a signal data due to vibration of a vehicle body and a living body signal. Accordingly, the above-described technology does not work precisely unless it is under a circumstances hard to receive the influence of vibration due to external factors, which raises problems in terms of practical utility.

A car air bag is not required to expand when a load body on the vehicle seat is not a person but a thing. If, during a collision, the air bag is expanded even though no one is seated but a thing put on the passenger seat, it results in wasteful repair costs. However, when a thing weighing prescribed load is put on the seat, conventionally, a method to automatically distinguish it between a thing and a person has not been known. A conventional method has been known whereby the amount of displacement of a spring supporting polyurethane foam as a cushioning material is measured, a weight sensor which detects the weight on the seat depending on the magnitude of the amount of displacement, a prescribed threshold value is established for the weight to distinguish between an adult and a child. However, even though such a weight sensor is used, if a thing has the prescribed load, motion of an air bag cannot be limited because the sensor judges it, for instance, as an adult.

The present invention has been made considering the above-described circumstances, and an object of the present invention is to provide a technology to simply and quickly analyze living body displacement signals collected from load bodies on a load body supporting means by a displacement signal collection sensor to quickly evaluate the living body state. Moreover, the present invention has another object of providing a technology suitable to reduce the effect of a noise signal due to external vibration caused by traveling of a car or the like, and to simply and precisely judge a load body state supported by a vehicle seat.

Means for Solving the Problem

The range of frequency of living body signals in a circulatory system such as brain waves or the like, concentrates in a zone of 10 Hz or less. That of respiration is 0.25 to 0.33 Hz, the number of heart beats 0.83 to 1.17 Hz, and the pulse wave 0.5 to 10 Hz. Therefore, as a countermeasure for a noise having a frequency zone of 10 Hz or more, provision of a low pass filter has been conventionally performed while obtaining information such as hardness of a blood vessel, blood viscosity or the like by analysis depending on the types of a wave form of the pulse wave. However, it is difficult to restrain the influence caused by noises at frequencies of 10 Hz or less, and therefore, the collecting site for the pulse wave analysis has to be limited.

A living body signal itself such as a pulse wave form, a breathing, or the like; vibration of muscles accompanying a pulse wave, a breathing, a body movement, a tremble, or the like; or vibration generated by properly superimposition on these factors (in the present invention, these are collectively referred to as a "living body displacement signal") have commonality in such that all they can be taken as a large wobbling-like vibration (wobbling vibration) which is typical of a living body, and are distinguished from external vibration having a relatively high frequency, which is inputted while traveling of a car. Then, on capturing these living body displacement signals under the circumstances of vibration generated from a car or the like, the present inventor thinks of using a rate of change (original waveform displacement inclination) in displacement (amplitude) for each arbitrary interval of signal data obtained by a displacement signal collection sensor. In other words, even when the original waveform of signal data undergoes large displacement by a sudden vibration generated by, for instance, asperities of a road surface, if a plurality of original waveform displacement inclination calculated for each arbitrary interval are used and treated them by every prescribed range of time, an inclination of the original waveform displacement due to noise signals is added and reduced to generate a canceled displacement (amplitude) inclination (average displacement inclination). Among the original waveforms of displacement (amplitude) of the living body displacement signal, for instance, there is the case where original waveform displacement inclination for each interval between a prescribed period of time is small though the amplitude is large, while, on the contrary, there is the case where the original waveform displacement inclination for each interval between the prescribed period of time is large though the amplitude is small. This is because pressure fluctuations due to factors excepting floor vibration, in other words, pressure fluctuation caused by receiving a living body displacement signal such as a pulse wave or a breathing are superimposed. Accordingly, the inventor has found that when time series fluctuation of such original waveform displacement inclination is collected, the above-described average displacement inclination from which large noise signals are removed is determined, and slide-calculation is further conducted under prescribed conditions using the average displacement inclination, then the wobbling-like fluctuation peculiar to a low-frequency living body signal which is difficult to obtain from the original waveform is emphasized so that the fluctuation tendency of the living body displacement signal can be actualized. In addition, this makes it possible to calculate more simply and quickly when compared with the case of analyzing a living body state by performing chaos analysis such as Lyapunov index as shown in Patent Documents 1 and 2, and a state including the type of a load body can be judged substantially in real time.

That is, the invention described in claim 1 is a load body state judging device to judge a state of a load body by analyzing signal data obtained from a displacement signal collection sensor which can collect a living body displacement signal of a load body supported by a load body supporting means, the load body state judging device including:

an average displacement inclination operating means to divide an original waveform of signal data obtained by the displacement signal collection sensor into each prescribed time range as an average displacement inclination;

an emphasis displacement inclination operating means to determine an emphasis displacement inclination by slide-calculating a rate of change of an average displacement inclination for each prescribed sampling time at a prescribed slide lap rate over a prescribed number of times from time series data of the average displacement inclination so that the time series data of the emphasis displacement inclination is obtained; and a state judging means to judge a load body state from the time series data of the emphasis displacement inclination obtained by the emphasis displacement inclination operating means.

The invention described in claim 2 provides the load body state judging device according to claim 1, in which the displacement signal collection sensor is attached to the load body supporting means.

The invention described in claim 3 provides the load body state judging device according to claim 1, in which the average displacement inclination operating means includes:

an original waveform displacement inclination operating means to divide an original waveform of signal data obtained by the displacement signal collection sensor into each prescribed time range, and further divide it within the prescribed time range into a plurality of intervals, and obtain a rate of change for each interval as an original waveform displacement inclination; and an original waveform displacement inclination summing means to sum up each original waveform displacement inclination obtained by the original waveform displacement inclination operating means, in which the sum up value obtained by the original waveform displacement inclination summing means is structured to be established as an average displacement inclination.

The invention described in claim 4 provides the load body state judging device according to claim 3, in which the original waveform displacement inclination operating means is structured to obtain the rate of change for each interval as the original waveform displacement inclination, taking the distance between respective intersecting points of an envelope on the upper limit side of the amplitude of an original waveform, an envelope on the lower limit side, or a curved line nearly parallel to any envelope, and the original waveform as an interval.

The invention described in claim 5 provides the load body state judging device according to claim 1, in which a sampling time interval used for slide-calculation of the emphasis displacement inclination operating means is 180 seconds, and a slide lap rate is 90%.

The invention described in claim 6 provides the load body state judging device according to claim 1, in which the state judging means includes at least any one of the type judging means to judge the type of the load body or a mental-and-physical state judging means to judge the mental-and-physical state when the load body is a person.

The invention described in claim 7 provides the load body state judging device according to claim 6, in which the mental-and-physical state judging means judges when the amplitude range of time series data of the emphasis displacement inclination gets relatively large compared with the amplitude before or after the range as a hypnagogic transition period between an awakening state and a sleeping state.

The invention described in claim 8 provides the load body state judging device according to claim 6, in which the type judging means includes a means to judge a load body to be a thing when the time series data of the emphasis displacement inclination are in transition within a prescribed range, and to be a person when in transition with an inclination change exceeding the prescribed range.

The invention described in claim 9 provides the load body state judging device according to claim 7, in which the type judging means includes a comparison means to read and compare a reference pattern of time series data of the emphasis displacement inclination stored in a storage unit in advance and specify an individual when the time series data of the emphasis displacement inclination are in transition with an inclination change exceeding a prescribed range.

The invention described in claim 10 provides the load body state judging device according to claim 1, in which the load body supporting means is a vehicle seat, and the displacement signal collection sensor is structured to be attached to at least any one portion out of a seat cushion, a seat back, or a headrest, and to detect pressure fluctuation based on a living body displacement signal of the load body.

The invention described in claim 11 provides the load body state judging device according to claim 10, in which the load body supporting means is a vehicle seat, and the displacement signal collection sensor is structured to be attached to at least any one portion of a seat cushion of the vehicle seat and to detect pressure fluctuation based on a living body displacement signal via the muscles of the buttocks of the load body.

The invention described in claim 12 provides the load body state judging device according to claim 1, in which the load body supporting means is a vehicle seat, and the displacement signal collection sensor is structured to detect a displacement amount of a member displacing based on a living body displacement signal of the load body.

The invention described in claim 13 provides the load body state judging device according to claim 12, in which the displacement signal collection sensor detecting a displacement amount of a member displacing based on a living body displacement signal of the load body serves as a load detection means to detect the load of the load body.

The invention described in claim 14 provides the load body state judging device according to claim 1, further including a load detection means detecting the load of the load body separately from the displacement signal collection sensor.

The invention described in claim 15 provides the load body state judging device according to claim 9, further including a load detection means detecting the load of a load body separately from the displacement signal collection sensor, and in which the comparison means compares the load of the load body obtained by the load detection means with a reference load stored in a storage unit in advance and to determine at least any one factor out of physique size, distinction of adult and child, and specification of an individual while adding the load to the comparison factors as one factor.

The invention described in claim 16 provides the load body state judging device according to claims 14 or 15, in which the load detection means is a displacement detection mechanism to detect a displacement amount of a member displacing based on the load of a load body out of the load body supporting means.

The invention described in claim 17 provides a vehicle seat, including:

a displacement signal collection sensor provided at least any one portion of a seat cushion, a seat back, and a headrest which are load body supporting units, and is able to collect displacement of the load body supporting unit due to a living body signal of the load body supported by the load body supporting unit; and a load body state judging device to analyze signal data obtained from the displacement signal collection sensor and judge the state of the load body, in which, the load body state judging device includes:

an average displacement inclination operating means to divide an original waveform of signal data obtained from the displacement signal collection sensor into each prescribed time range and to determine a rate of change of the signal data in the prescribed time range as an average displacement inclination;

an emphasis displacement inclination operating means to obtain a rate of change of an average displacement inclination for each prescribed sampling time period from time series data of the average displacement inclination by slide calculating at a prescribed slide lap rate over prescribed number of times as the emphasis displacement inclination so as to obtain time series data of the emphasis displacement inclination; and a state judging means judging a load body state from time series data of the emphasis displacement inclination obtained by the emphasis displacement inclination operating means.

The invention described in claim 18 provides the vehicle seat according to claim 17, in which the load body supporting unit includes:

a vibration-removal mechanism having a small spring constant in an equilibrium state; and a cushioning mechanism arranged to provide with a spring characteristic closely analogous to the spring characteristics of a human muscle, in which the displacement signal collection sensor is disposed between the vibration-removal mechanism and a cushioning mechanism.

The invention described in claim 19 provides the vehicle seat according to claim 18, in which the displacement signal collection sensor is disposed between a base cushioning material disposed in a seat cushion and included in the vibration-removal mechanism and a surface layer cushioning material strained on a cushion frame disposed in a seat cushion and included in the cushioning mechanism, and is able to collect a living body displacement signal via the muscles of the buttocks.

The invention described in claim 20 provides the vehicle seat according to claim 17, in which the average displacement inclination operating means of the load body state judging device includes:

an original waveform displacement inclination operating means to divide an original waveform of signal data obtained from the displacement signal collection sensor into each prescribed time range, and further divide it within the prescribed time range into a plurality of intervals, and obtain a rate of change for each interval as an original waveform displacement inclination; and an original waveform displacement inclination summing means to sum up each original waveform displacement inclination obtained by the original waveform displacement inclination operating means, in which the sum up value obtained by the original waveform displacement inclination summing means is structured to be established as an average displacement inclination.

The invention described in claim 21 provides the vehicle seat according to claim 20, in which the original waveform displacement inclination operating means of the load body state judging device is structured to obtain the rate of change for each interval as the original waveform displacement inclination, taking the distance between respective intersecting points of an envelope of the upper limit side of the amplitude of an original waveform, an envelope on the lower limit side, or a curved line nearly parallel to either envelope, and the original waveform as an interval.

The invention described in claim 22 provides the vehicle seat according to claim 17, in which a sampling time interval used for slide-calculation of the emphasis displacement inclination operating means included in the load body state judging device is 180 seconds, and a slide lap rate is 90%.

The invention described in claim 23 provides the vehicle seat according to claim 17, in which the state judging means of the load body state judging device includes at least any one means out of a type judging means to judge the type of the load body and a mental-and-physical state judging means to judge the mental-and-physical state when the load body is a person.

The invention described in claim 24 provides the vehicle seat according to claim 23, in which the mental-and-physical state judging means judges when the amplitude range of time series data of the emphasis displacement inclination gets relatively large compared with the amplitude before or after the range as a hypnagogic transition period between an awakening state and a sleeping state.

The invention described in claim 25 provides the vehicle seat according to claim 23, in which the type of judging means includes a means to judge a load body to be a thing when the time series data of the emphasis displacement inclination are in transition within a prescribed range, and to be a person when in transition with an inclination change exceeding the prescribed range.

The invention described in claim 26 provides vehicle seat according to claim 17, further including a load detection means detecting the load of a load body.

The invention described in claim 27 provides the vehicle seat according to claim 23, further including a load detection means detecting the load of a load body and in which the comparison means compares the load of the load body obtained by the load detection means with a reference load stored in a storage unit in advance to judge at least any one factor out of physique size, distinction between an adult and a child, and identification of an individual while adding the load to the comparison factors as one factor.

The invention described in claim 28 provides a computer program to analyze signal data obtained from a displacement signal collection sensor which is able to collect a living body displacement signal of the load body supported by the load body supporting means and to make a computer execute a process for judging a load body state, the computer program including:

an average displacement inclination operating step to divide an original waveform of signal data obtained by the displacement signal collection sensor into each prescribed time range and determine a rate of change of the signal data in the prescribed time range as an average displacement inclination;

an emphasis displacement inclination operating step to determine an emphasis displacement inclination for each prescribed sampling time at a prescribed slide lap rate over a prescribed number of times from time series data of the average displacement inclination so that the time series data of the emphasis displacement inclination is obtained; and a state judging step to judge a load body state from time series data of the emphasis displacement inclination obtained by the emphasis displacement inclination operating step.

The invention described in claim 29 provides the computer program according to claim 28, in which the average displacement inclination operating step includes:

an original waveform displacement inclination operating step to divide an original waveform of signal data obtained by the displacement signal collection sensor into each prescribed time range, and further divide it within the prescribed time range into a plurality of intervals, and obtain a rate of change for each interval as an original waveform displacement inclination; and an original waveform displacement inclination summing step to sum up each original waveform displacement inclination obtained by the original waveform displacement inclination operating step, in which the sum up value obtained by the original waveform displacement inclination summing step is structured to be established as an average displacement inclination.

The invention described in claim 30 provides the computer program according to claim 29, in which the original waveform displacement inclination operating step is structured to obtain the rate of change for each interval as the original waveform displacement inclination, taking the distance between respective intersecting points of an envelope on the upper limit side of the amplitude of an original waveform, an envelope on the lower limit side, or a curved line nearly parallel to any envelope, and the original waveform as an interval.

The invention described in claim 31 provides the computer program according to claim 28, in which a sampling time interval used for slide-calculation of the emphasis displacement inclination operating step is 180 seconds, and a slide lap rate is 90%.

The invention described in claim 32 provides the computer program according to claim 28, in which the state judging step includes at least any one step out of a type judging step to judge the type of the load body and a mental-and-physical state judging step to judge the mental-and-physical state when the load body is a person.

The invention described in claim 33 provides the computer program according to claim 32, in which the mental-and-physical state judging step judges when the amplitude range of the time series data of the emphasis displacement inclination getting relatively large compared with the amplitude before or after the range as in a hypnagogic transition period between an awakening state and a sleeping state.

The invention described in claim 34 provides the computer program according to claim 32, in which the type judging step includes a means to judge the load body as a thing when the time series data of the emphasis displacement inclination are in transition within a prescribed range, and as a person when in transition with an inclination change exceeding the prescribed range.

EFFECT OF THE INVENTION

According to the present invention, the load body state judging device is structured such that a rate of change of an original waveform of displacement signal data of a load body supported by a load body supporting means per arbitrary interval is determined as an original waveform displacement inclination, time series data of an average displacement inclination for a prescribed time range is determined from a plurality of the original waveform displacement inclination, and further, an emphasized displacement inclination is determined by slide calculating the time series data of the average displacement inclination for each prescribed sampling time to judge a state of the load body from the time series data of the emphasis displacement inclination thus obtained.

Accordingly, for instance, even when vibration or the like transmitted from a road surface during traveling of a car is included in displacement signal data collected by a displacement signal collection sensor, it is possible to obtain time series data in which a wobbling-like fluctuation (wobbling) peculiar to a low frequency living body displacement signal is emphasized by determining the emphasis displacement inclination from the original waveform displacement inclination and the average displacement inclination as described above.

Moreover, by defining a relation between a fluctuation tendency of the time series data of the emphasis displacement inclination obtained in this manner and a state of a living body in advance, it is possible to judge the state of a living body, for instance, whether it is in a awakening state, a sleeping state, or in a transition state (hypnagogic transition period) between the awakening state and the sleeping state, from this fluctuation tendency.

Furthermore, when "a thing" is on a load body supporting means, a fluctuation signal by a living body displacement signal is not superimposed on the displacement signal data collected by a displacement signal collection sensor. Accordingly, when the time series data of the above-described emphasis displacement inclination are determined, since no wobbling-like fluctuation (wobbling) peculiar to the living body signal occurs, it is possible to judge it as "a thing".

In addition, when a load detection means is attached, a living body displacement signal (dynamic load fluctuation) due to a body movement is detected in the case of the load body being "a person", whereas in the case of the load body being "a thing", such a load fluctuation does not occur. Therefore, the type of the load body can be judged more precisely. Further, when a load body is judged as "a person", it is possible to judge physique size, or the distinction between an adult and a child by considering the load detected by the load detection means.

BRIEF DESCRIPTION OF DRAWINGS

FIGS. 6A to 6C are block diagrams showing variations of a state judging means;

FIG. 12A is the case of varying a sampling time while setting a slide lap rate at 90%, and FIG. 12B is the case of varying the slide lap rate while setting the sampling time for 180 seconds.

FIG. 29 is a view showing another example of a displacement detecting mechanism provided with an exciting coil and a pick up coil to a torsion bar;

FIG. 33A is a view showing time series data of an emphasis displacement inclination of a fingertip volume pulse wave in test example 3, and FIG. 33B is a view showing time series data of the emphasis displacement inclination of a living body displacement signal via the muscles of the buttocks;

FIG. 34 is data showing a comparison between the fingertip volume pulse wave and the brain wave measured in test example 4.

BEST MODE FOR CARRYING OUT THE INVENTION

Figure 1:
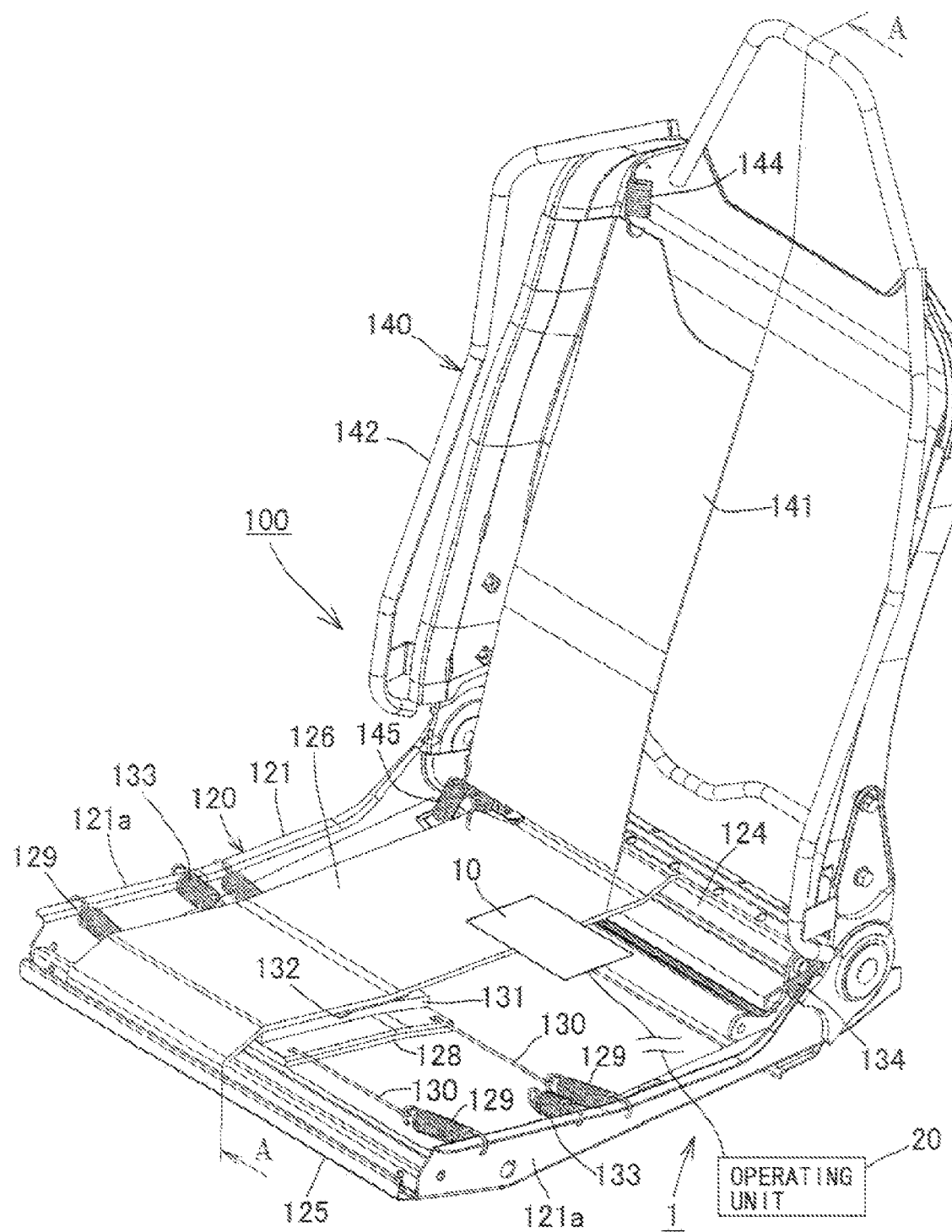
FIG. 1 is a perspective view showing a schematic structure of a seat attached with a load body state judging device relating to an embodiment of the present invention.
Figure 2:
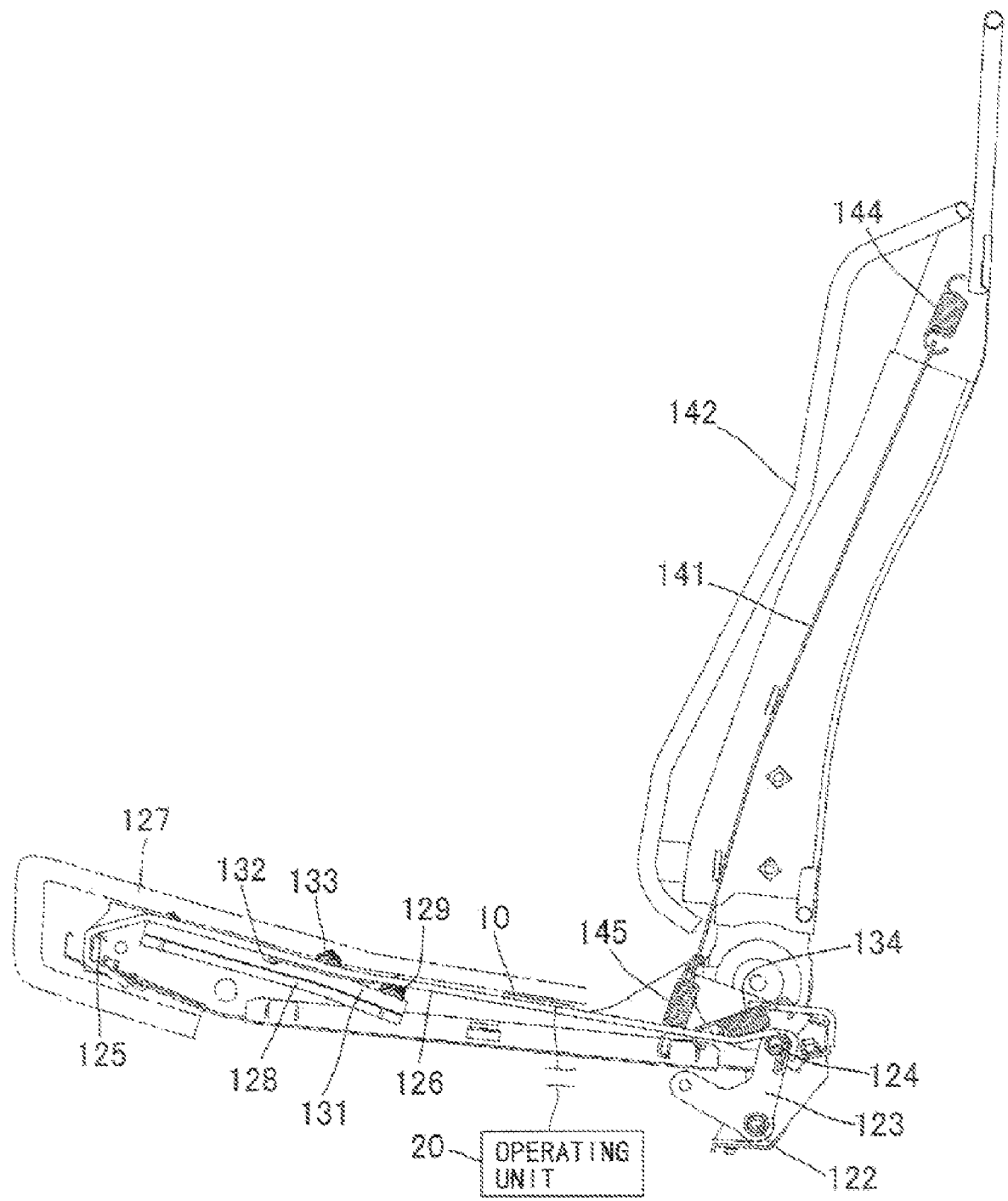
FIG. 2 is a side view showing a schematic structure of the seat.
Figure 3:
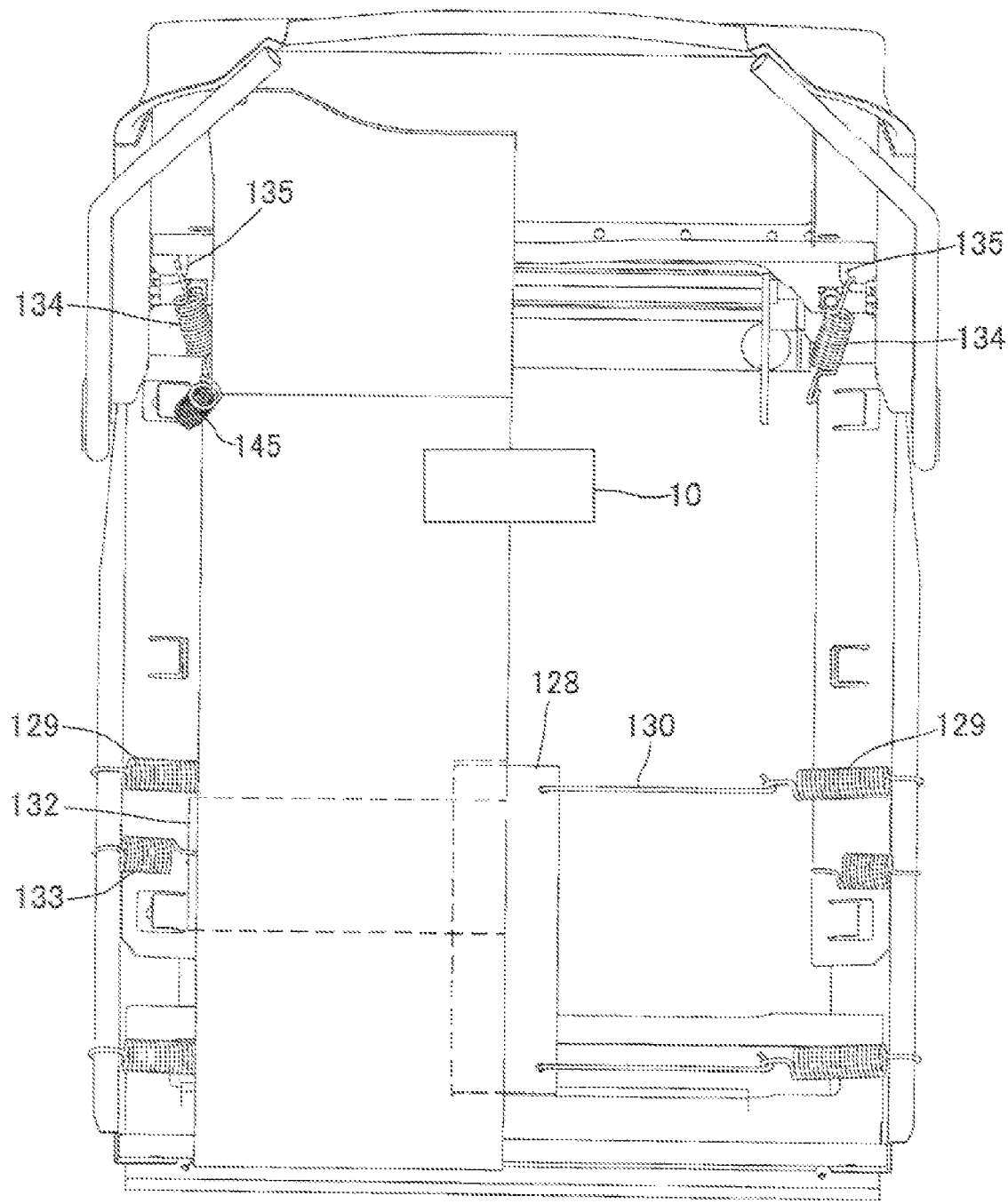
FIG. 3 is a plane view showing a schematic structure of the seat.

The present invention will be explained hereinafter more in detail based on embodiments shown in drawings. FIG. 1 to FIG. 3 are views of the schematic structure in a state of attaching a load body state judging device 1 relating to an embodiment of the present to a vehicle seat 100 of a car or the like which is a load body supporting means. The load body state judging device 1 has an operating unit 20 which receives and analyzes signal data collected by a displacement signal collection sensor 10.

A pressure sensor can be used as the displacement signal collection sensor 10. However, since it is attached to, at least, one of a seat cushion, a seat back or a headrest, it is necessary not to let a person feel something foreign at the time of being seated. Therefore, it is preferable to use, for instance, a film piezoelectric device. As the film piezoelectric device, it is possible to use, for instance, a product name: PIEZO FILM LDT series, Product Number: LDT 4-028K/L manufactured by TOKYO SENSOR Co. Ltd. Though the displacement signal collection sensor 10 can be attached to at least any of the seat cushion, the seat back or the headrest as described above, it is desirable to make up a structure by attaching displacement signal collection sensor 10 to the seat cushion which comes in contact with a human body all the time, and to detect a living body displacement signal (wobbling) spreading through the buttocks pulse wave, a breathing, a movement of the pelvis, a body movement, or the like via the muscles of the buttocks. Further, it is allowable to dispose only on sheet of the displacement signal collection sensor 10 in the vicinity below the ischium node, since the buttocks might get out of the detectable range of the sensor by taking, for instance, a posture of shifting the buttocks forward (sacrum posture) during seating for a long time, it is also adoptable to dispose one more or a plurality sheets of sensors in front of back a little thereof in addition to the sensor disposed in the vicinity below the ischium node.

It should be noted that when collecting a living body displacement signal from the seat 100 of a car or the like, usage of the above-described pressure sensor is preferable because the living body displacement signal can be collected as a body surface vibration spreading through in the muscle only by being seated without attaching a special measurement device on a person. However, when conducting detection of a hypnagogic omen or fatigue analysis by a mental-and-physical state judging means (mental-and-physical state judging step) 23a to be described later, it is preferable to collect a living body signal itself such as a brain wave or a breathing for signal data having less noise as a living body displacement signal. For instance, when conducting an experiment such as performance evaluation of a seat or a suspension while letting a person be seated on a passenger seat of a car or when using it for living body evaluation of a patient in a hospital or the like, since there is no harm in driving a car or the like, it is effective even when taking such a structure. In this event, for instance, an optical fingertip pulse wave meter collecting a well-known fingertip volume pulse wave or a measuring equipment to collect an earlobe pulse wave, or the like can be used as a displacement signal collection sensor.

The structure of the seat 100 is no limited, but it is preferable that respective cushioning structures of a seat cushion 120 and a seat back 140 can transmit slight pressure fluctuation of the muscle produced by a breathing, a heartbeat (pulse wave), a body movement, or the like of a person to the displacement signal collection sensor 10, and at the same time, it is provided with an excellent floor vibration removal function. FIGS. 1 to 3 show an example of desirable seat 100 provided with such a performance.

The seat cushion 120 of this seat 100 is provided with a torsion bar 122 at the rear of a cushion frame 121, a rear supporting frame 124 is supported to an arm 123 biased in a backward tilting direction by the torsion bar 122, and a base cushioning material 126 to be strained between a front supporting frame 125 and the rear supporting frame 124. At an upper portion of the base cushioning material 126, a surface layer cushioning material 127 strained on the cushion frame 121 at a low tension is provided as shown with an imaginary line in FIG. 2. Note that the base cushioning material 126 and the surface layer cushioning material 127 can be formed with each one sheet of cushioning material, or can be formed by laminating a plurality of cushioning materials as necessary.

The displacement signal collection sensor 10 is provided between the base cushioning material 126 and the surface layer cushioning material 127. Since the base cushioning material 126 has a structure such that a tension is given by an elastic force of the torsion bar 122, the floor vibration can be removed. Accordingly, transmission of the vibration to the surface layer cushioning material 127 is reduced. On the other hand, since the surface layer cushioning material 127 is strained by the cushion frame 121 at a low tension, pressure on the muscle of a person (especially on the muscle of the buttocks) is small at the time of seating, expansion and contraction movement of the blood vessel, and muscle movement caused by a breathing or body movement can not be disturbed. Accordingly, mixing of the external vibration noises to the signal data collected by the displacement signal collection sensor 10 is reduced so that a pressure fluctuation signal caused by a living body displacement signal can be collected more precisely.

The surface layer cushioning material 127 can be prepared with a two-dimensional net member or a thin urethane material, but in order to lessen pressure on the muscles of the buttocks or the like, it is preferable that the spring characteristic at the time of straining the surface layer cushioning material 127 on the cushion frame 121 is closely analogous to the spring characteristic of the muscles of the buttocks or the like as much as possible. As the surface layer cushioning material 127 having such a characteristic, it is desirable to use a solid knitted fabric with a small reaction force disclosed, for instance, in Japanese Patent Application Laid-open No, 2002-336076. Such a solid knitted fabric is prepared using, for instance, a Double Raschel knitting machine or the like, and is formed by reciprocating a connecting yarn between a pair of ground knitted fabrics disposed at a prescribed distance. A two-dimensional net member, a solid knitted fabric or the like can be used for the base cushioning material 126, similarly to the surface layer cushioning material 127.

Figure 4:
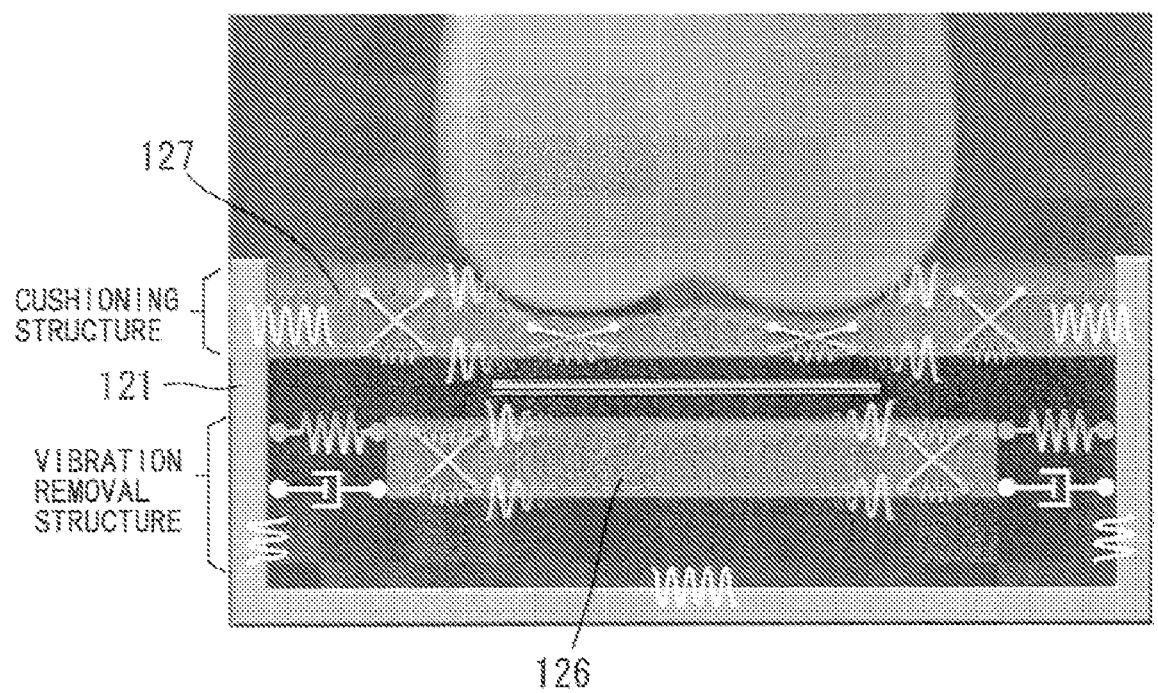
FIG. 4 is a schematic diagram showing preferable positions of arrangement of a displacement signal collection sensor.

In other words, the displacement signal collection sensor is, as schematically shown in FIG. 4, preferably disposed between a vibration-removal mechanism having almost no increase or decrease of the load at a prescribed displacement amount range in a balanced state of a person in being seated, that is, a so-called zero spring constant range as a static spring characteristic due to an elasticity of a spring member such as the torsion bar 122 or the like and a damping characteristic of the base cushioning material 126 or the like made of a solid knitted fabric or the like; and a cushioning mechanism having a spring characteristic not to press the muscles, closely analogous to the spring characteristic of the muscles of the buttocks, and similarly to that of the surface layer cushioning material 127 made of a solid knitted fabric or the like strained on the cushion frame 121.

It should be noted that a vibration-removal mechanism having a range of zero spring constant is not limited to those prepared from a combination of the torsion bar 122 and the base cushioning material 126 as in the present embodiment, but it is possible to prepare from a seat suspension or the like using a vibration-removal mechanism, which is structured of the combination of the repulsive and attractive force of a permanent magnet and an elastic member such as a metal spring or the like, and has a region of spring constant nearly zero in an equilibrium point of the load mass, as disclosed in Japanese patent Application Laid-open No. 2003-139192 or Japanese Patent Application Laid-open No. 2002-206594 proposed by the present applicant.

In addition, since the base cushioning material 126 is strained between the rear supporting frame 124 and the front supporting frame 125 as described above, and the surface layer cushioning material 127 is strained on the cushion frame 121 so as to cover the base cushioning material 126, it is desirable to provide a structure supplementing a restoration force at the time of removing a load. As such a structure, in FIGS. 1 to 3, a metal board or a hard supplement board 128 made of plastic or the like is arranged under the base cushioning material 126 in nearly central or in the front end side and elastically supported via the coil spring 129 and wire 130 supported at an end by the side frame 121a, and further a member laminated of shock absorbing materials such as urethane or a solid knitted fabric on the upper surface of the supplement board 128 is provided. Furthermore, an belt-like elastic member 132 made of rubber or the like is disposed in the width direction between the sock absorbing material 131 and the base cushioning material 126, and supported with a coil spring 133 supported by the side frame 121a at an end thereof. Further, an end of a coil spring 134 is hung on a portion of the base cushioning material 126 at a position corresponding to the vicinity of both side portions of the rear supporting frame 124, and the other end of the coil spring 134 is engaged with a supplement frame member 135 positioned in the direction extending diagonally outside in the back. The tension is generated in the longitudinal direction on the base cushioning material 126 by the coil spring 134 arranged at the rear, and a tension intersecting the longitudinal direction of the tension is generated at the same time by the belt-like elastic member 132 or the like, and thus, the restoration force is supplemented. Moreover, the supplement board 128 is disposed close to the front of the base cushioning material 126, which enhances the holdability and a feeling of stability, and improves also a function of posture-supporting faculty.

The seat back 140 includes a base cushioning material 141 and a surface layer cushioning material (not shown) strained on a back frame 142 so as to cover the base cushioning material 141. The base cushioning material 141 and the surface layer cushioning material are formed using a solid knitted fabric or the like similarly to those used for the above-described seat cushion 120. The base cushioning material 141 is supported by a coil spring 144 to the upper portion of the back frame 142 at the upper end thereof, and is supported by a coil spring 145 to the cushion frame 121 at the lower end thereof, so that a prescribed tension is given to ensure restoration ability at the time of load-removal.

Figure 5:
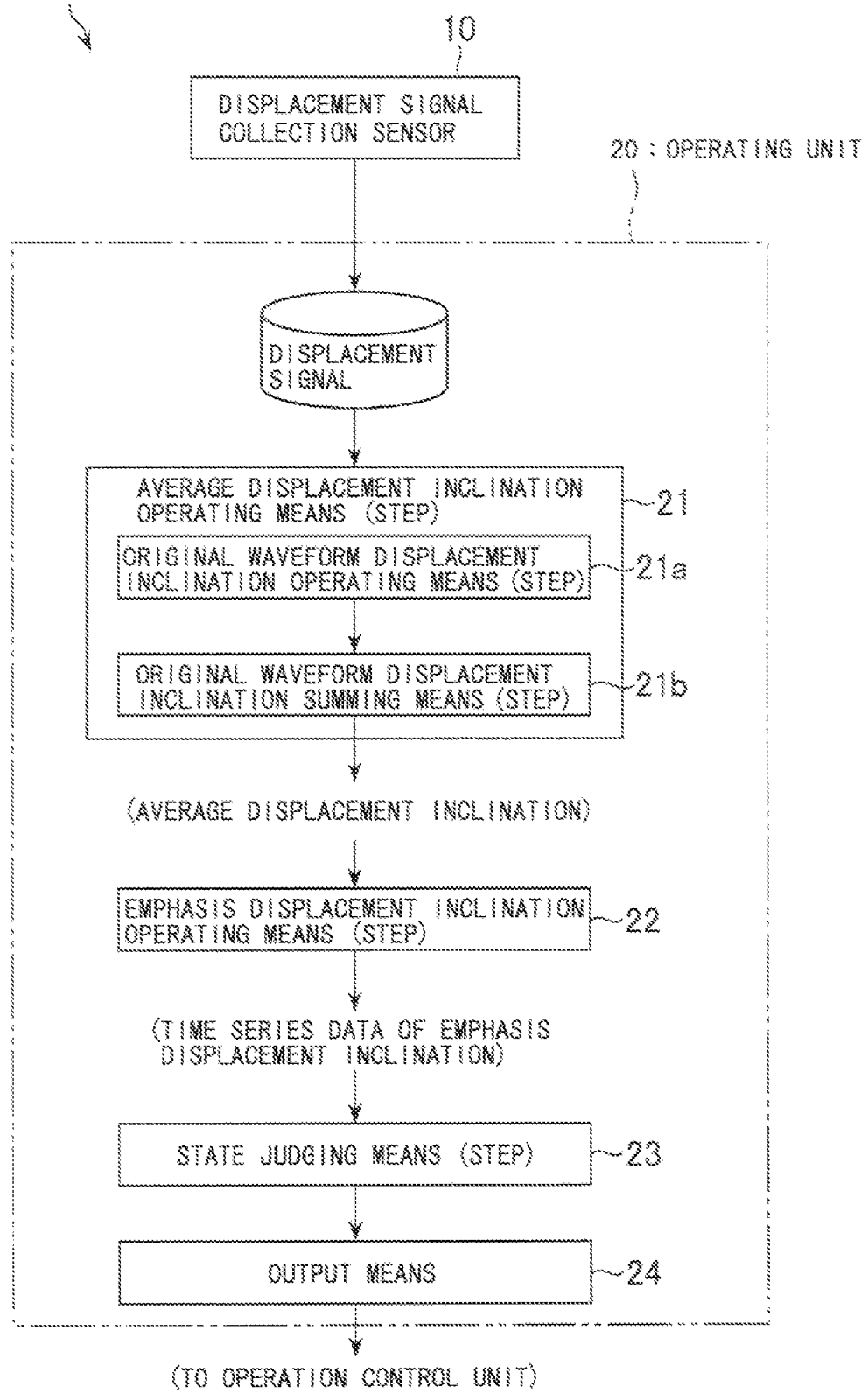
FIG. 5 is a block diagram showing a schematic structure of a load body state judging device relating to the embodiment.

The operating unit 20 is connected to the displacement signal collection sensor 10 via a radio or a signal cable, and includes an average displacement inclination operating means (average displacement inclination operating step) 21, an emphasis displacement inclination operating means (emphasis displacement inclination operating step) 22, and a state judging means (state judging step) 23 as a program as shown in FIG. 5.

The average displacement inclination operating means (average displacement inclination operating step) 21 is a means to divide an original waveform into each prescribed time range which is set in advance (for instance, per 5 seconds), to determine an average rate of change of the displacement (amplitude) of signal data in the prescribed time range, so as to obtain it as the average displacement inclination. By determining the average displacement inclination, the effect of noise signals becomes small even if they are contained in the original means 21 is not limited so far as it has such a function, it is preferable to have a structure including the following original waveform displacement inclination operating means 9 original waveform displacement inclination operating step) 21a and the original waveform displacement inclination summing means 21b, because it can be easily calculated and easily cancel the effect of the noise signals.

Figure 7:
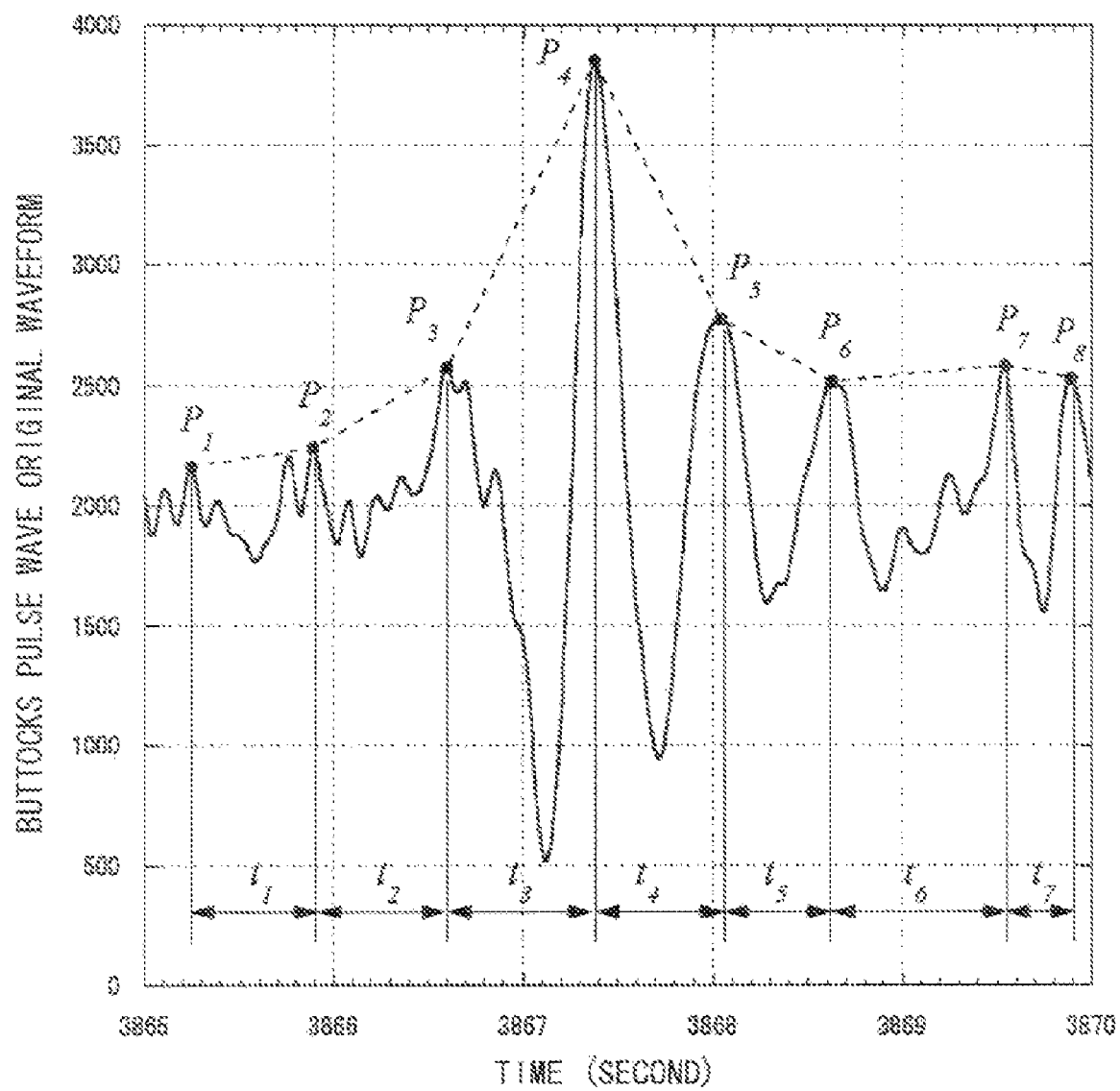
FIG. 7 is a view to explain a calculation method of an average displacement inclination.

The original waveform displacement inclination operating means (original waveform displacement inclination operating step) 21a is a means to determine a rate of change of the displacement (amplitude) for every interval divided further into a plurality of intervals within the above-described prescribed time range as an original waveform displacement inclination. The number of intervals is not limited, and it is possible to define, for instance, an interval between respective intersection points of the upper limit side envelope of the original waveform and the original waveform to be a unit of the interval. FIG. 7 is a view showing one example thereof, and adjacent intersection points between the upper side envelope of the amplitude and the original waveform, that is intervals between P1 and P2, between P2 and P3 . . . between P7 and P8 become one interval respectively. The original waveform displacement inclination is determined by obtaining the difference in value of the respective intervals, that is, between P1 to P2, P2 to P3 . . . P7 to P8, and by dividing them with the time of the respective intervals, t1 seconds, t2 seconds . . . t7 seconds. It should be noted that in order to establish respective intervals, for instance, it is possible to conduct detection using a prescribed threshold value, preferably using a 70% of the fluctuation width of the waveform in respect to the magnitude of displacement (amplitude) of the waveform using a smoothing differentiation method on signal data by Savitzky and Golay, so that respective peak values on the upper limit side are calculated, and a rate of change between respective peak values can be calculated as an original waveform displacement inclination. However, respective peak values calculated in this manner are nearly coincident with the intersection points (P1 to P8) of the envelope of the amplitude on the upper limit side and the original waveform.

As the calculation means of an original waveform in addition to this means, it is possible to determine an interval between adjacent intersection points of an envelop on the lower limit side and an original waveform as one interval, or to determine an interval between adjacent intersection points of a curve nearly parallel to an envelope of the upper limit side or the lower limit side and an original waveform as one interval. When a line crossing nearly center of the amplitude of an original waveform is taken as a base line, if base line shaking occurs in which the base line does not become a straight line but a curved line, the base line shaking is canceled and reformed to be a straight line, or a new straight line conforming to the lower limit of the amplitude is established and the above-described original waveform displacement inclination is determined.

In the original waveform displacement inclination summing means (original waveform displacement inclination summing step) 21b, respective original waveform displacement inclination obtained by the original waveform displacement inclination operating means 21a is totaled for each of the above-described prescribed time ranges to establish this value as an average displacement inclination. Accordingly, in the case in FIG. 7, $$\text{Average displacement inclination} = \sum_{1 \to ?}^{n} \frac{P_{n+1} - P_n}{t_n} \quad \text{[Equation 1]}$$

In FIG. 7, the point P4 is a noise signal. By determining this as above, the inclination between P3 and P4 gets a large plus value, while the inclination between P4 and P5 is a large minus value. Accordingly, by totaling these, the effect of the noise signal is almost canceled.

Figure 8:
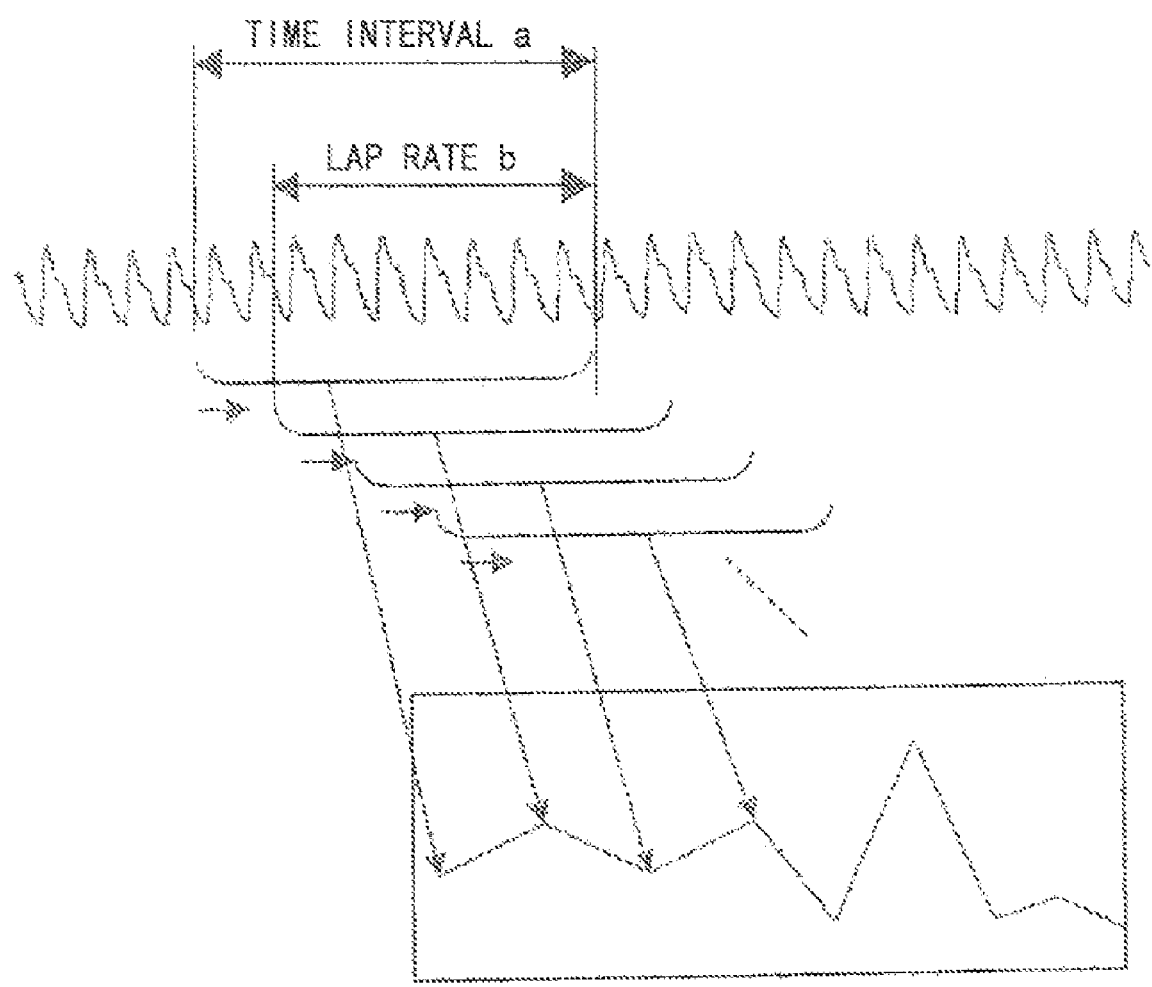
FIG. 8 is a view to explain a slide calculation method.

The emphasis displacement inclination operating means (emphasis displacement inclination operating step) 22 uses a value of respective average displacement inclination for each prescribed time range obtained from the average displacement inclination operating means 21 and calculates a rate of change of an average displacement inclination of the average displacement inclination value for each prescribed sampling time by slide calculation at the prescribed slide lap rate over the prescribed number of times to establish the emphasis displacement inclination (refer to FIG. 8). The slide calculation is carried out as follows.

For instant, when the emphasis displacement inclination during a lapse of T seconds (s) is determined at a slide lap rate of 90%, first, using respective average displacement inclination values for each prescribed time range (for instant, per 5 seconds), the rate of change between 0 (s) and T (s) is determined using the least-squares method or the like. Then, the rate of changes of respective average displacement inclinations in the following period;

Slide calculation (1): between T/10(s) and T+T/10(s)
Slide calculation (2): between 2×T/10(s) and T+2×T/10(s)
Slide calculation (n): between n×T/10(s) and T+n×T/10(s)

are determined using the least-squares method.

Then, the time series data of the emphasis displacement inclination are determined by plotting the value of the rate of change (emphasis displacement inclination) of the average displacement inclination value obtained first at the point of T(s), and by plotting the emphasis displacement inclination value obtained by the next slide calculation at the point of T+T/10(s), and by plotting the emphasis displacement inclination value obtained by n-th slide calculation at the point of T+n×T/10(s).

Here, 180 seconds is most suitable for the sampling time (T seconds) when conducting the slide calculation to determine the emphasis displacement inclination, and 90% is most suitable for the slide lap rate. This is obtained from the result of conducting a sleeping experiment for 30 minutes under the same circumstance with several testees, and analyzing the fingertip volume pulse waves obtained from the testees. FIG. 9A to FIG. 12B show an example thereof.

Figure 11A:
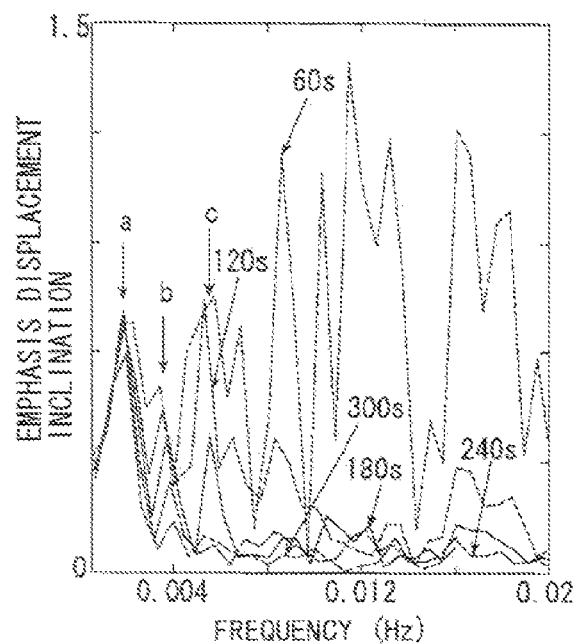
FIGS. 11A is a view showing the results of a frequency analysis in FIGS. 9A to 9E.
Figure 11B:
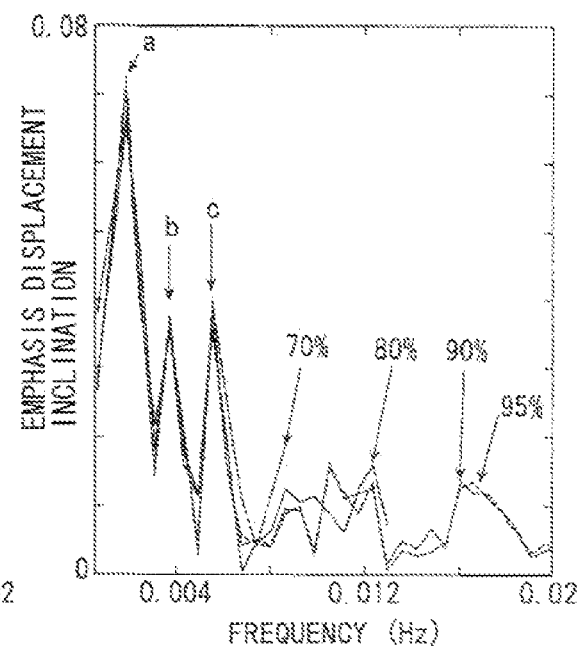
FIG. 11B is a view showing the results of a frequency analysis in FIGS. 10A to 10D.

FIGS. 9A to 9E are time series data of the emphasis displacement inclination in which the sampling time intervals for inclination calculation are set to be 60 seconds, 120 seconds, 180 seconds, 240 seconds and 300 seconds, and the slide lap rate is unified to 90%, and FIG. 11A shows the result of the frequency analysis thereof. Note that the symbol "a" and "b" in the drawings are the amplitudes of characteristic signals appeared during hypnagogic transition period, "a" shows the amplitude of a characteristic hypnagogic omen signal appeared before the testee starts to fall asleep, and "b" shows the amplitude of a signal in a transition state from appearance of signs of the hypnagogic omen to falling asleep. "c" shows the amplitude of a sleep signal when entering into sleep. The judgment whether it is in an awakening state or a sleeping state was determined by measuring a manner fluctuation period of time (for instant, the time of starting a doze, or the time of falling asleep) of the testee taken from data during observation and taking video by a third party, and referring to the time series data of the emphasis displacement inclination.

In each case, from time series signals of the respective omen signals (here, a hypnagogic omen signal a, transition state signal b, and a sleep signal c), the peak value coefficient of a discrete signal of the inclination: Cf=Xp/Xs (where Xp indicates the maximum amplitude of the omen signal, while Xs indicates the amplitude of a normal state signal before or after generating the omen signal) is determined to find a condition of showing the characteristics of the inclination in its best sensitivity from the value. The result is shown in FIG. 9F, and it is found from the drawing that the time interval 180 seconds is best in sensitivity as a time interval for the inclination calculation, The reason to set the means value to be 180 seconds is because the command launching frequency of muscle activity due to fatigue is carried much by a peripheral reflection mechanism in the muscle. In other words, it is expect that it related to a phenomenon that the command of muscle activity decreases owing to attenuation of the higher level central excitation caused by fatigue and participation of the peripheral suppressive reflection mechanism, but when the blood stream is restored to normal, the central excitation level is restored within 180 seconds.

Figure 10A:
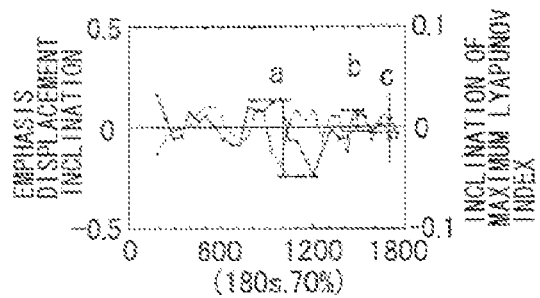
FIGS. 10A to 10D are views showing emphasis displacement inclinations when a slide lap rate is changed in order to conduct the most suitable inclination calculation in a sleep experiment for 30 minutes.
Figure 10B:
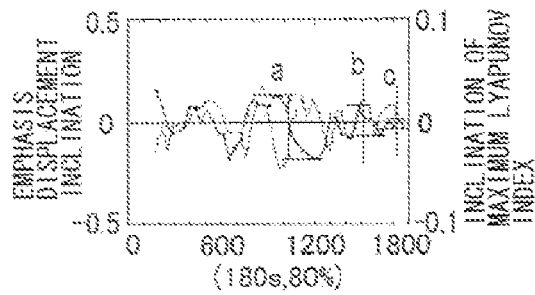
Figure 10C:
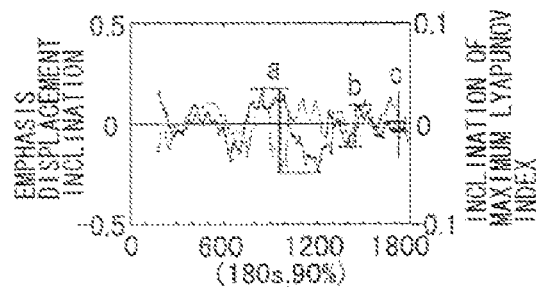
Figure 10D:
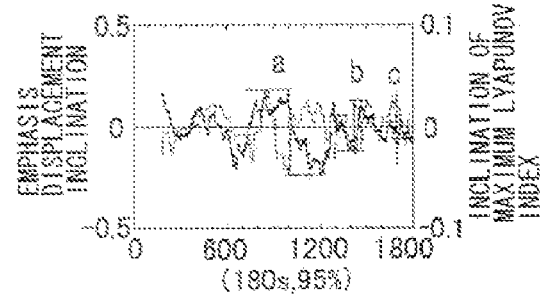
Figure 10E:
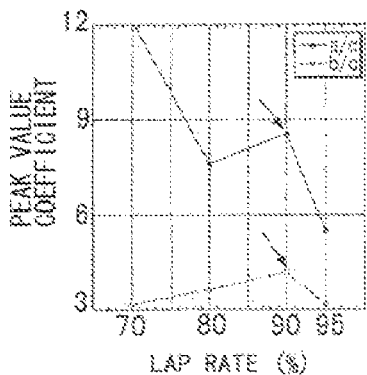
FIG. 10E is a view showing a peak value coefficient.

Whereas, the slide lap rate is calculated from 70% to 95% in the case of 180 seconds sampling time interval. Values less than 70% are omitted because the time series signal becomes thinly. The result is shown in FIGS. 10A to 10D, and FIG. 11B shows the result of analyzing the frequency. This graph shows that the noise was low when the slide lap rate was at 90% and 95%, but found the highest sensitivity at the slide lap rate of 90%, referring to the graph in FIG. 10E showing the peak value coefficient thereof. Thus, the most preferable condition for extracting information characteristics for a living body is time interval of 180 seconds and a slide lap rate of 90% which can clearly pick up the omen signals a, b, and c.

Figure 12A:
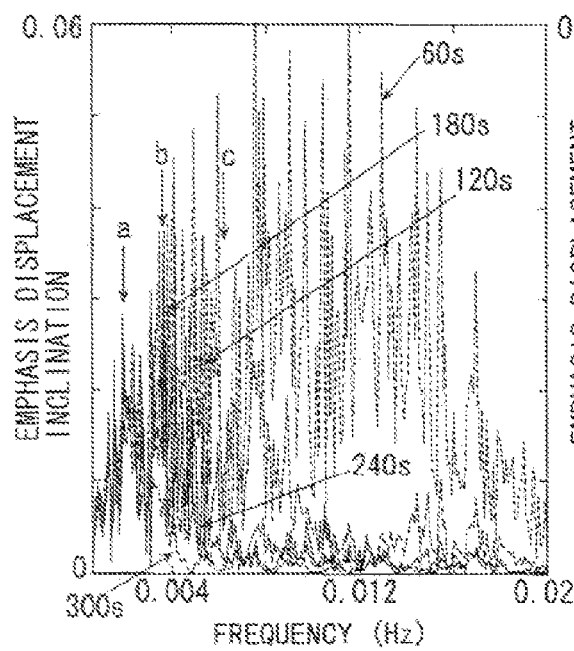
FIGS. 12A and 12B are views showing the results of a frequency analysis of an emphasis displacement inclination obtained by a sleep experiment for 180 minutes.
Figure 12B:
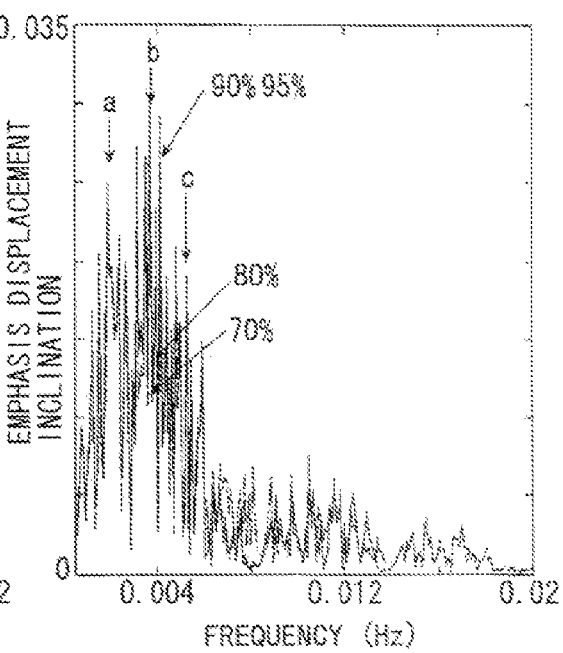

The above-described result is the case of 30 minutes experiment, but when taking 180 minutes for the experiment, the characteristics of the omen signals a, b, and c can be extracted also at the time interval of 180 seconds and slide lap rate of 90%, as shown in FIGS. 12A and 12B.

From the result described above, for the emphasis displacement inclination operating means 22, it is most suitable to determine the rate of change of respective average displacement inclination for the time interval of 180 seconds using the least-squares method, and then, to determine the inclination for the time interval of 180 seconds, taking 18 seconds later as a starting point using the least-squares method. In other words, the time interval for conducting the inclination calculation is set to be 180 seconds, and the slide lap rate is set to be 90%, the wobbling-like characteristic (wobbling) peculiar to a living body displacement signal can be remarkably extracted.

The frequency band of a circulatory system living body signal concentrates here to a frequency band of 10 Hz or less. It corresponds to 0.25 to 0.33 Hz for a breathing, 0.83 to 1.17 Hz for the number of heartbeat, and 0.5 to 10 Hz for a brain wave. The conventional brain wave analysis copes with providing a low pass filter for the noises of the frequency band of 10 Hz or more, obtaining information on the hardness of the blood vessel, blood viscosity, or the like by analysis according to the waveform type of a brain wave. However, it is difficult to restrain the effect due to mixing of noises having a frequency band of 10 Hz or less, which limits a collection site of the brain wave analysis. On the other hand, a living body displacement signal such as brain wave, a breathing, a body movement or the like collected in a circumstance of generating vibration of a car is generally a vibration excited by an irregular vibration source, it is not practical for extracting a pressure fluctuation signal caused by a living body vibration of a driver unless the effect of noise due to the irregular vibration source is minimized. However, by conducting the above-described processing to obtain the time series data for emphasis displacement signal can be extracted placing too much emphasis thereon, and the effect on the noise can be minimized.

The state judging means (state judging step) 23 judges a state of a load body based on the time series data of an emphasis displacement inclination obtained by the emphasis displacement inclination operating means 22. More concretely, as shown in FIG. 6, the state judging means 23 includes at least either one out of the mental-and-physical state judging means (mental-and-physical state judging step) 23a to judge the mental-and-physical state, and the type judging means (type judging step) 23b to judge the type of a load body when the load body is a person.

The mental-and-physical state judging means 23a judges that the range of amplitude of time series data of the emphasis displacement inclination becomes relatively larger compared with the amplitude before or after the range is a hypnagogic transition period between awakening state and a sleeping state. From the experimental result shown in FIGS. 9A to 9F and FIGS. 10A to 10E, the amplitude in a prescribed time range before sleeping shows a characteristic signal to become relatively larger compared with the amplitude in a range before the range (awakening state) and after the range (sleeping state). Accordingly, the characteristic signal with the amplitude getting larger is recognized as a hypnagogic omen signal, and judges it a hypnagogic transition period when such a signal is generated. The magnitude of an amplitude at the time of judging to be a hypnagogic omen signal is preferably twice or more compared with those in the before range or the after range. This is because when the sleeping experiment shown in FIGS. 9A to 9F and FIGS. 10A to 10E is carried out for 32 adult men and women, almost all of them showed amplitudes of twice or more.

Figure 9A:
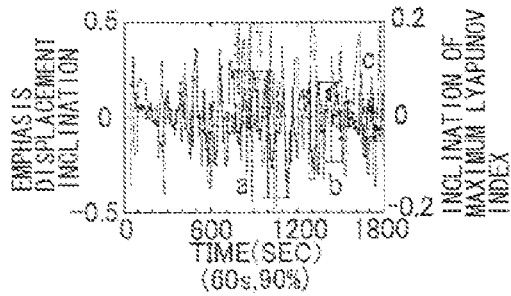
FIGS. 9A to 9E are views showing emphasis displacement inclinations when a sampling time is changed in order to perform the most suitable calculation of inclination in a sleep experiment for 30 minutes.
Figure 9B:
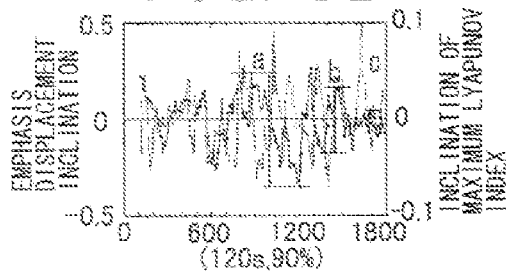
Figure 9C:
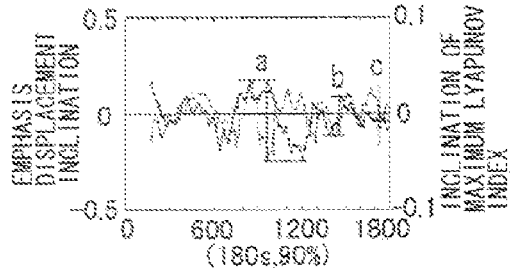
Figure 9D:
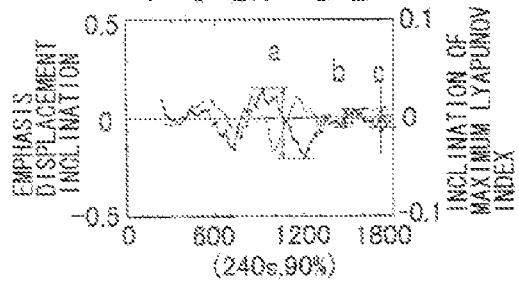
Figure 9E:
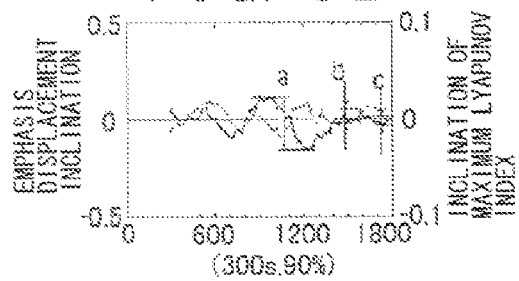
Figure 9F:
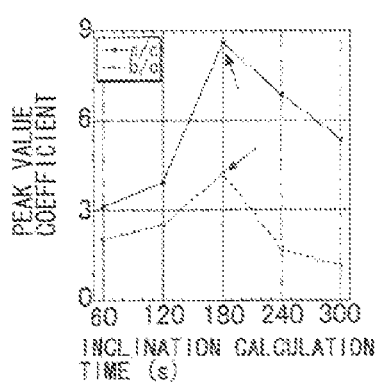
FIG. 9F is a view showing a peak value coefficient.

Note that in FIGS. 9A to 9F and FIGS. 10A to 10E, a maximum Lyapnov index which is a chaos index is calculated together, and the time series data of the maximum Lyapunov index inclination calculated by slide calculation of the maximum Lyapunov index using the same method as the above-described emphasis displacement inclination operating means are also shown. The maximum Lyapunov index is said to show mainly a change in the mental state of a person, but the result in FIG. 9C shows that in a hypnagogic transition period during which a hypnagogic omen signal or a transition state signal appears, there is a relation of 180 degrees opposite in phase between the time series changes of the emphasis displacement inclination and the maximum Lyapunov index. Accordingly, in order to determine the hypnagogic transition period more precisely, it is preferable to carry out operation of time series data of the maximum Lyapunov index inclination and display them together with time series data of the emphasis displacement inclination so that judgment whether or not such an opposite phase state exists is preferably used as a determination index.

The type judging determining means 23b judges the case when time series data of the emphasis displacement inclination are within a prescribed range to be a thing, and when they are running with an inclination change exceeding the prescribed range to be a person. As described above, by calculating the average displacement inclination and the emphasis displacement inclination, external vibration noises are reduced, the time series data of the emphasis displacement inclination serve as those grasping the fluctuation due to a living body displacement signal. Therefore, the time series data of the emphasis displacement inclination in the case where a load body is "a thing" and no living body displacement signal is generated are those having an extremely small temporal change without generation of wobble. Therefore, when a prescribed threshold value is established, and the temporal change of the emphasis displacement inclination is within a predetermined range, it is judged as "a thing". When a temporal change exceeding the prescribed range is found, since it is a fluctuation due to a living body displacement signal, it is judged to be "a person".

Only one of the mental-and-physical state judging means 23a or the type judging means 23b may be included in a configuration according to the usage as shown in FIGS. 6A and 6B. However, when a seat is for a car among vehicle seats, since the frequency to appear both cases when a person is seated on the seat and when a thing is placed is relatively high, it is desirable to include both the mental-and-physical state judging means 23a and the type judging means 23b, as shown in FIG. 6C.

An output means 24 outputs a result of the above-described state judging means 23 and transmits it to a prescribed control unit. For instance, when a hypnogogic omen signal is detected by the mental-and-physical state judging means 23a, the output result is transmitted to a control unit of an appropriate awakening means to awaken by exciting at least one of the five senses and allows it to function. For instance, it is possible to awaken by operating a warning device, or by slanting a seat back slightly. When it is judged as "a thing" by the type of judging means 23b, for instance, a signal to cancel the operation is sent to a control unit of an airbag.

It should be noted that a computer program of the present invention, which includes the above-described average displacement inclination operating means (average displacement inclination operating step) 21, the emphasis displacement inclination operating means (emphasis displacement inclination operating step) 22; and the mental-and-physical state judging state (mental-and-physical state judging step) 23a and the type judging means (type judging step) 23b composing the state judging means (state judging step) 23 and the like can be provided by storing it in a storage medium. The term "storage medium" is a medium to carry a program which can not occupy a space by itself, and is, for instance, a flexible disc, a hard disc, a CD-ROM, an MO (optical magnetic disc), a DVD-ROM or the like. It is also possible to transmit to another computer from a computer installing a program relating to the present invention via a communication line. It is also possible to compose the present invention by pre-installing or down-loading the above-described program to a general-purpose terminal device.

TEST EXAMPLE 1

(Noise Signal Removal Confirmation Test)

A seating experiment was carried out for the case when a seat 100 attached with a pressure sensor as the displacement signal collection sensor 10 between the base cushioning material 126 and the surface layer cushioning material 127 of the seat cushion 120 as shown FIGS. 1 to 3 is installed under a circumstance of without external vibration (static state), and the case of installing it on a vibrator (dynamic state). A solid knitted fabric is used as the base cushioning material 126, and a solid knitted fabric strained on a cushion frame at an elongation rate of less than 5% is used as the surface layer cushioning material 127. Other configurations are as described-above. The testee was a healthy Japanese male in his age of 30's, and pressure sensor data for respective states of static state and dynamic state were collected while the testee was seated for 30 minutes. In a dynamic state, vibration was made with a random vibration including a protrusion climbing over, which generates impulsive vibration of 2.0 G in term of P-P value in amplitude at 1.3 Hz, and is collected using a wagon in Michigan in US.

Figure 13:
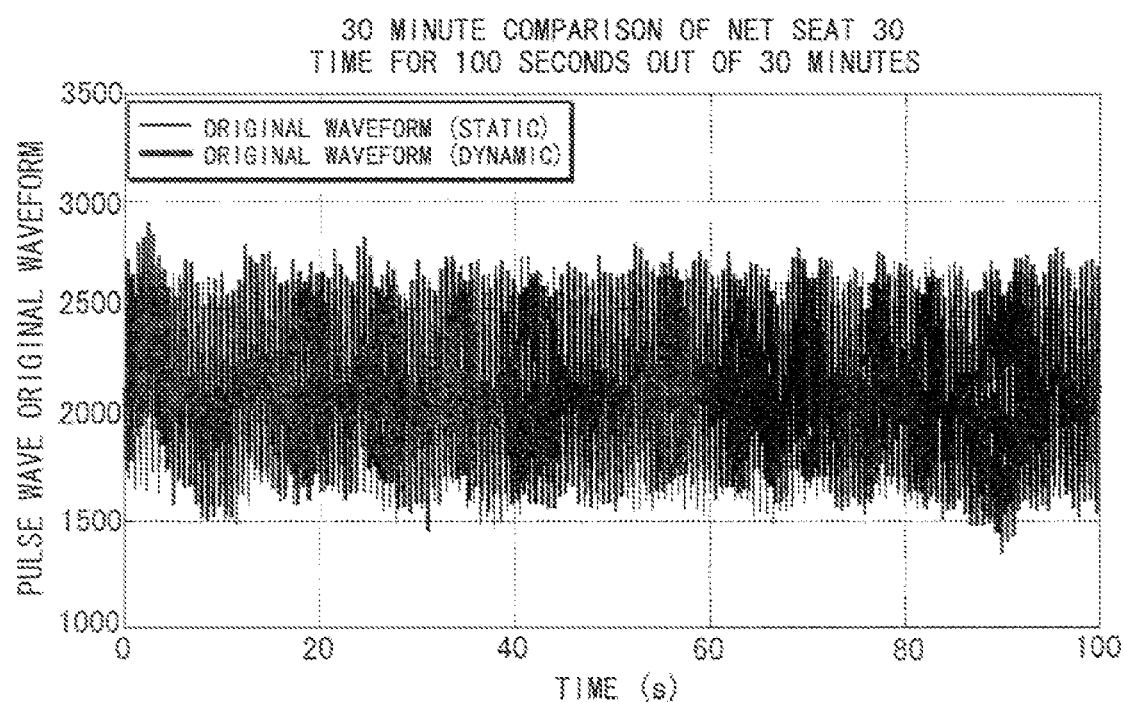
FIG. 13 is a view showing original waveforms of data obtained by a pressure sensor for each of a static state and a dynamic state in test example 1.
Figure 14:
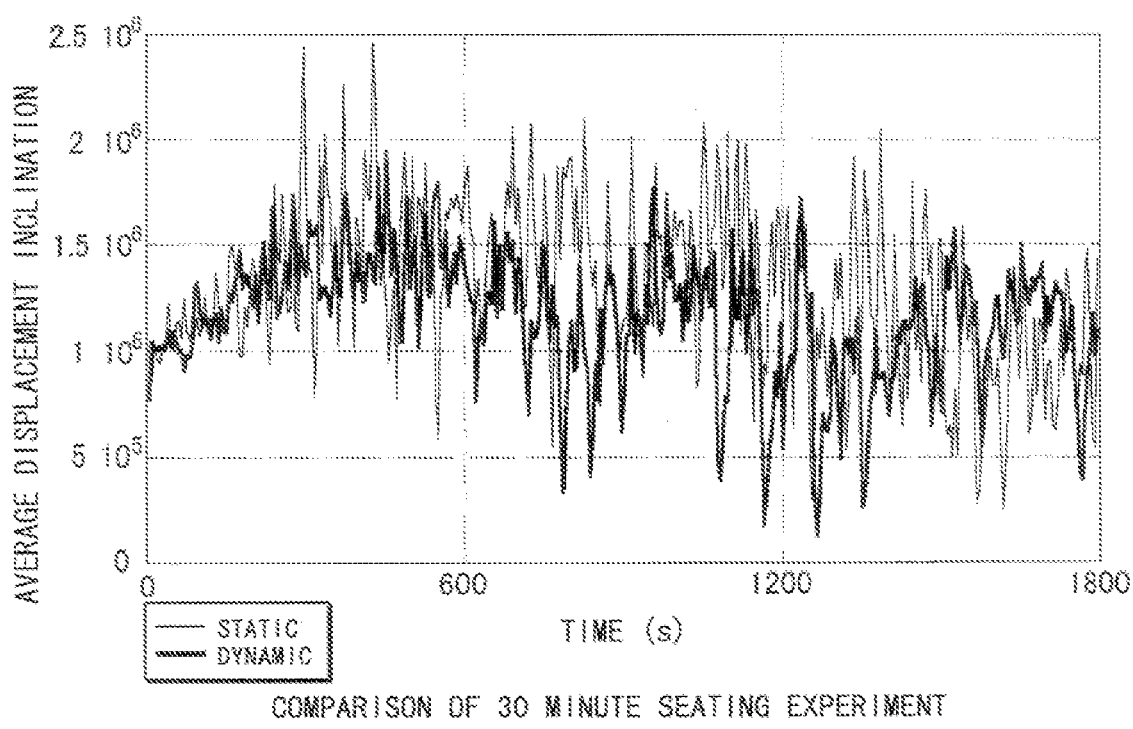
FIG. 14 is a view showing time series data of the average displacement inclination calculated by an average displacement inclination operating means based on the original waveform in FIG. 13.
Figure 15:
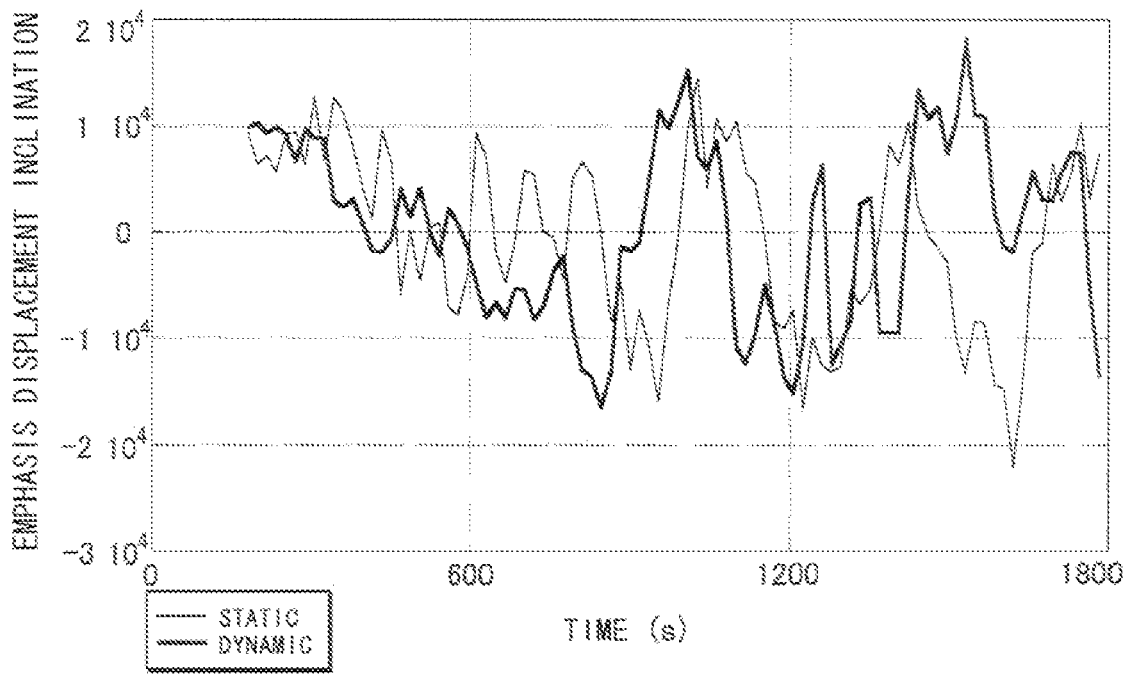
FIG. 15 is a view showing a time series change of the emphasis displacement inclination calculated by further processing with an emphasis displacement inclination operating means.

The result is shown in FIG. 13. FIG. 13 shows an original waveforms of the data obtained from a pressure sensor for the static state and the dynamic state respectively. FIG. 14 shows time series data of the average displacement inclination calculated by the average displacement inclination operating means 21 based on the original waveform obtained by the pressure sensor. FIG. 15 shows time series change of the emphasis displacement inclination processed and calculated by the emphasis displacement inclination operating means 22. As shown from these drawings, it is extremely difficult to specify the characteristics of the detected signal data using the original waveform. An external vibration noises are included in the dynamic state data. On the other hand, in the dynamic state data of the time series data in the average displacement inclination in FIG. 14, the effect on the external vibration noise is reduced by the average displacement inclination operating means 21, but it is difficult to judge the approximity of both data when compared with the static state data. However, in the time series data of the emphasis displacement inclination shown in FIG. 15, data in a static state and those in a dynamic state are closely analogous to each other. It is found that the present invention is suitable for reducing the effect of noise signals due to external vibration to extract vibration of a body surface (living body displacement signal) via the muscle of a crew member of a car, which is caused by a brain wave, a breathing, a body movement or the like.

Figure 16:
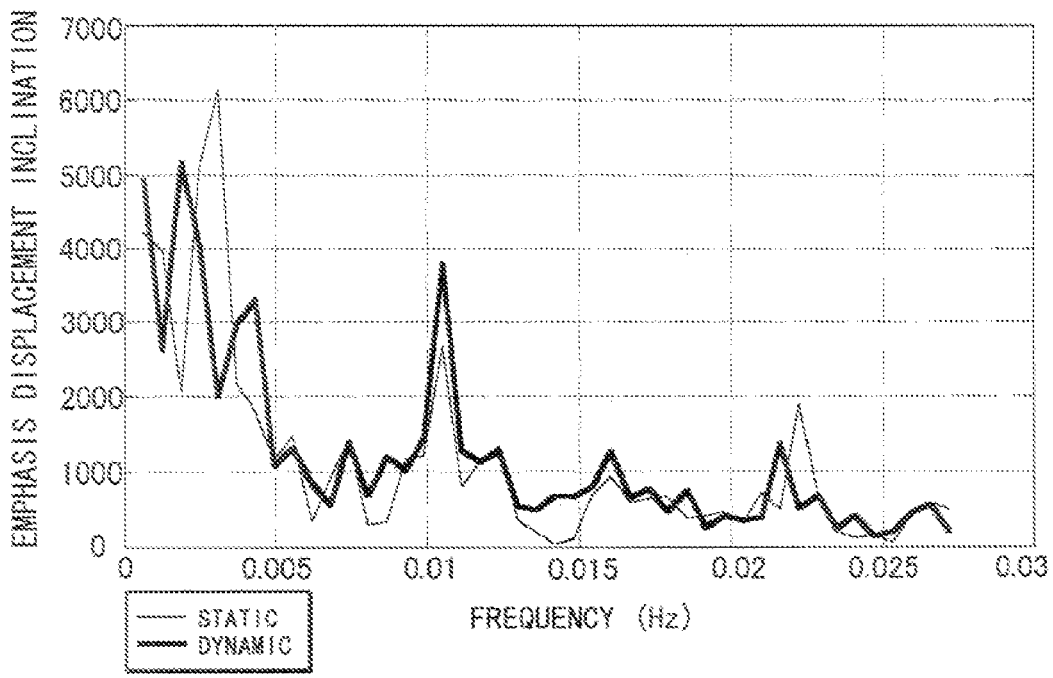
FIG. 16 is a view showing a result of the frequency analysis for the emphasis displacement inclination in FIG. 15.

It was also confirmed from the result obtained in FIG. 15 that results of the frequency analysis in a static state and in a dynamic state are nearly coincident as shown in FIG. 16.

TEST EXAMPLE 2

(Sleeping Test While Seated)

(1) Actual Car Test

Traveling in a city was carried out while a seat similar to that used in the test example 1 was installed on a passenger seat of a car and a testee was seated on it. Here, an optical fingertip pulse wave meter was installed in the car and a fingertip volume pulse wave of the testee, not vibration of the muscles of the buttocks by a pressure sensor, was collected as a living body displacement signal. Then, a relation between time series data of the emphasis displacement inclination of the fingertip volume pulse wave and the mental-and-physical state was studied. An observer was seated on the rear seat, and observed a state change of the testee. The testee was a healthy Japanese female in her age of 30's. The result is shown in FIG. 17 to FIG. 19.

Figure 17:
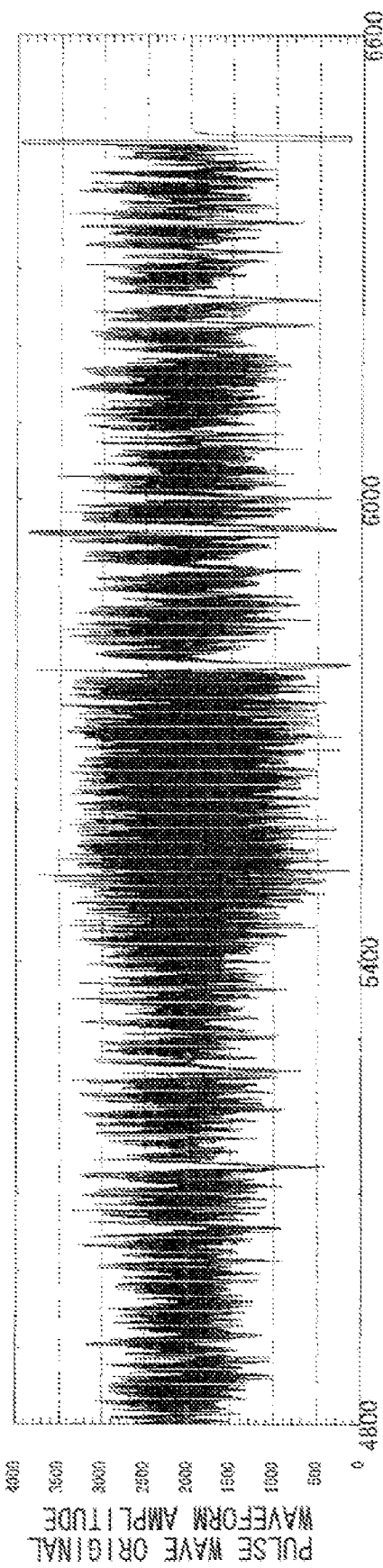
FIG. 17 is a view showing the original waveform of a fingertip volume pulse wave measured with an actual car test in test example 2.
Figure 18:
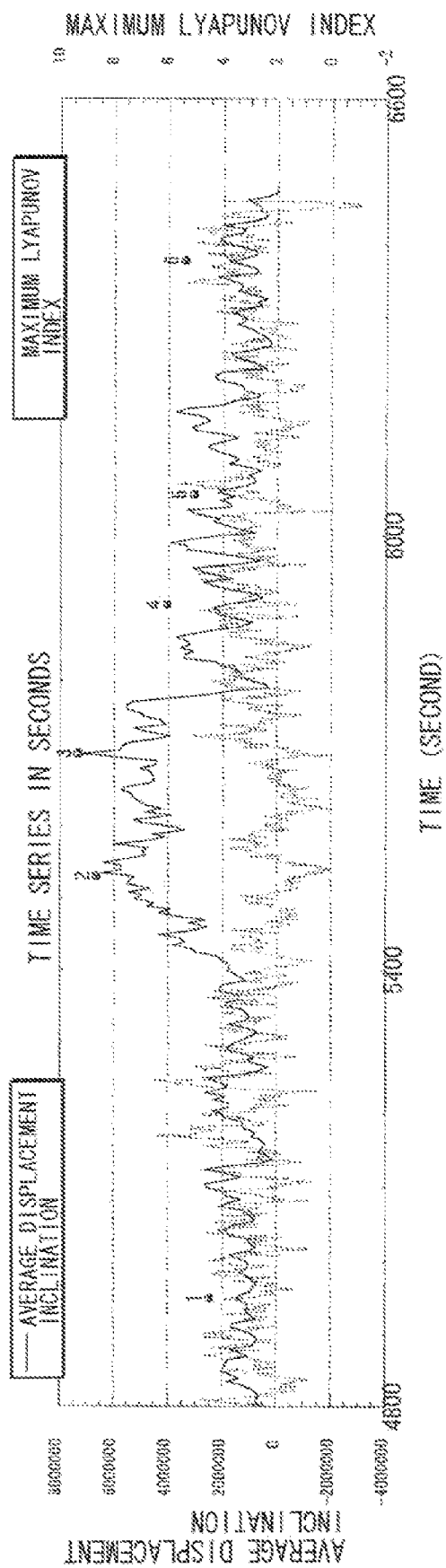
FIG. 18 is a view showing time series data of an average displacement inclination of the actual car test in test example 2.
Figure 19:
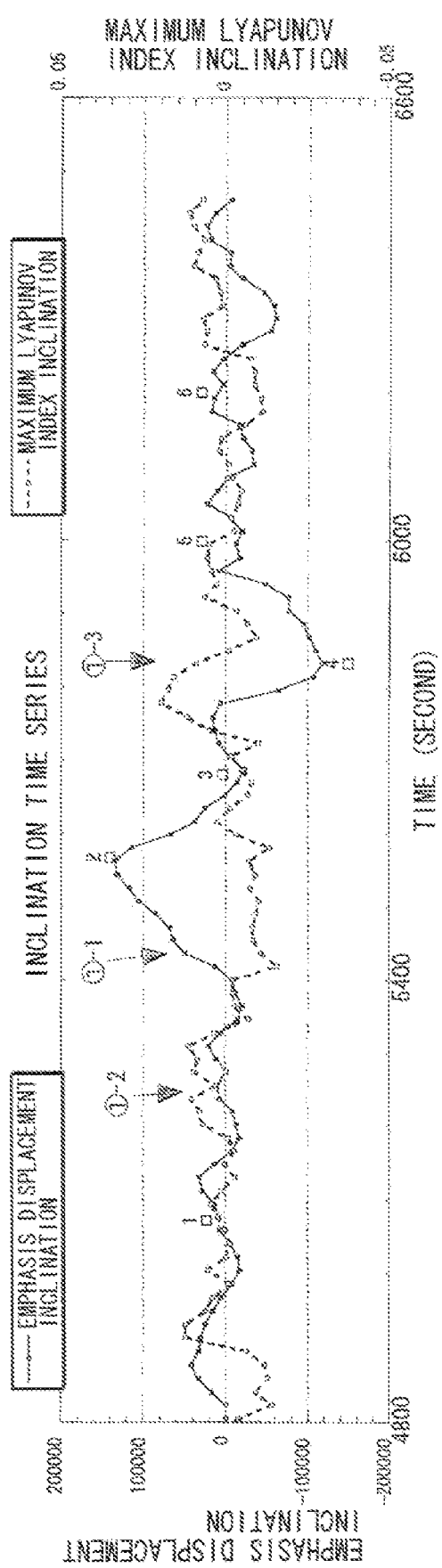
FIG. 19 is a view showing time series data of an emphasis displacement inclination of the actual car test in test example 2.

FIG. 17 shows the original waveform of the fingertip volume pulse wave, FIG. 18 shows the time series data of the average displacement inclination, and FIG. 19 shows the time series data of the emphasis displacement inclination. In the case of this testee, it is found that a large wobbling is generated in both the original waveform and the time series data of the average displacement inclination, which shows that living body displacements signals are collected. Whereas the time series data of the emphasis displacement inclination in FIG. 19 shows even to the extent that a hypnagogic omen signal peculiar to a hypnagogic transition period showing a change of twice or more is generated in the vicinity of 5400 seconds to 6000 seconds compared with the amplitude before and after the peak zone. From the time series data of the emphasis displacement inclination in FIG. 19, judgment is made such that point 1 shown by a numeral in the drawing is an awakening state, point 2 to point 4 are in a hypnagogic transition period, and point 5 to point 6 are in a sleeping state, and comparing them with the observation results by the observer, they show an extremely good agreement.

In FIG. 18, a maximum Lyapnov index which is a chaos index is calculated together and shown as the time series data, and in FIG. 19, the time series data of the maximum Lyapunov index inclination calculated by slide calculation of the maximum Lyapunov index time series data using the same method as the above-described emphasis displacement inclination operating means are shown. As a result, as opposite phase relation between the time series data of the emphasis displacement inclination and the time series data of the maximum Lyapunov index inclination is found in the vicinity from 5400 seconds to 5600 seconds, which is confirmed as a hypnagogic transition period.

(2) Static Seating Test

A similar seat to that used in Test Example 1 was set in a laboratory, a testee was seated and a fingertip volume pulse wave was collected for 30 minutes and a relation between the time series data of the emphasis displacement inclination and the mental-and-physical state was studied. A change in a state of the testee was observed by an observer in this test. The testee was healthy Japanese male in his age of 20's. The result is shown in FIG. 20 to FIG. 22.

Figure 20:
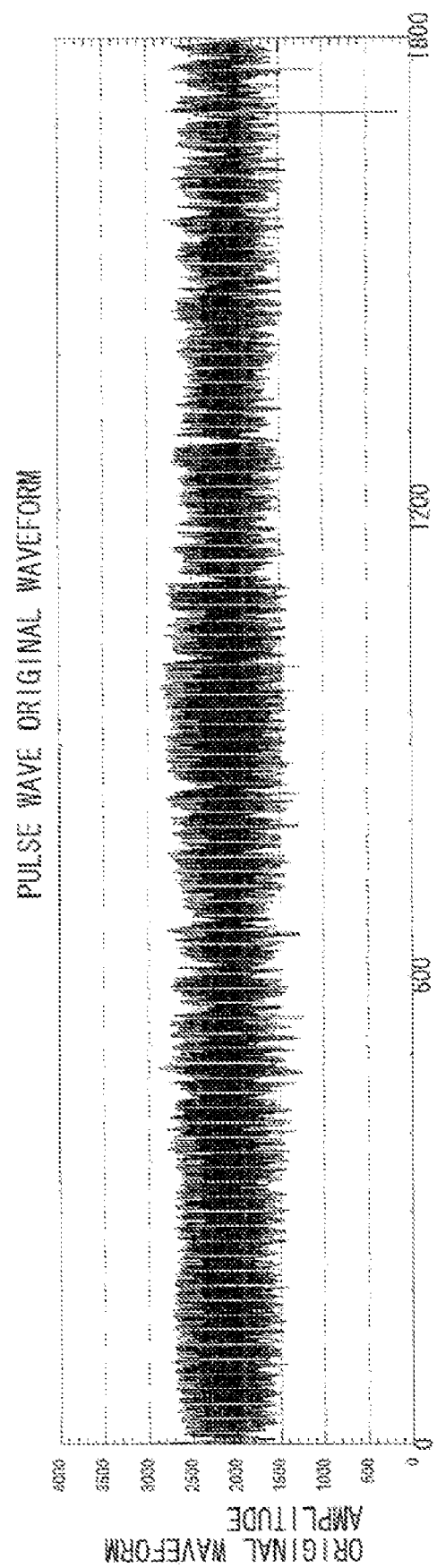
FIG. 20 is a view showing the original waveform of the fingertip volume pulse wave measured by a static seating test in test example 2.
Figure 21:
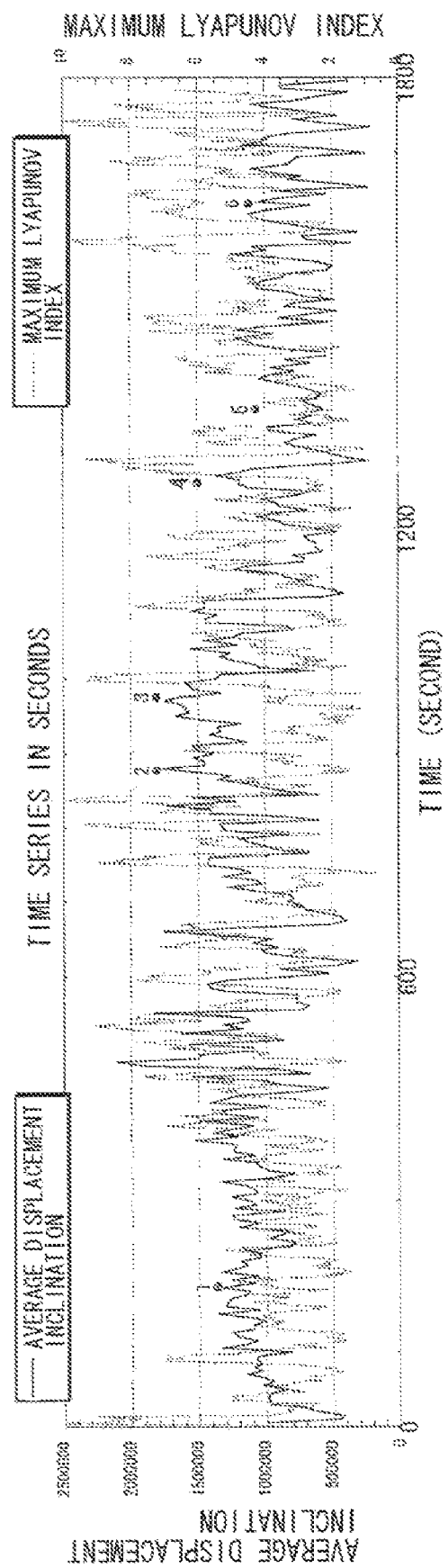
FIG. 21 is a view showing time series data of the average displacement inclination of the static seating test in test example 2.
Figure 22:
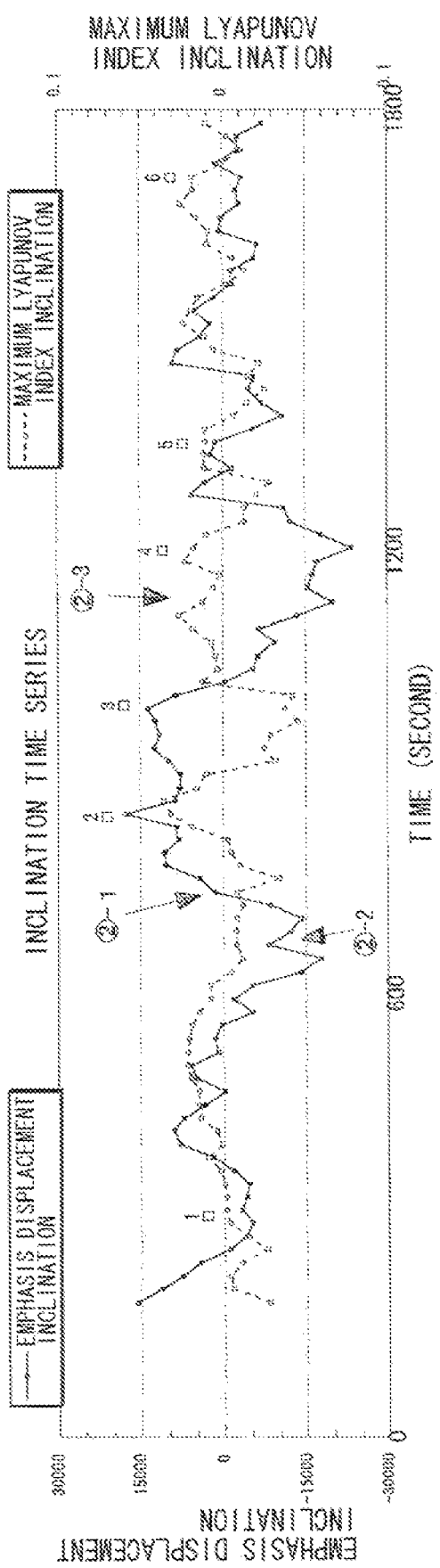
FIG. 22 is a view showing time series data of the emphasis displacement inclination of the static seating test in test example 2.

FIG. 20 shows an original waveform of a fingertip volume pulse wave, FIG. 21 shows the time series data of an average displacement inclination, and FIG. 22 shows time series data of an emphasis displacement inclination. In the case of this testee, it is difficult to capture wobbling from the original waveform. The amplitude of the time series data of the average displacement inclination in FIG. 21 is also unstable, which makes it difficult to judge at what timing the change of the mental-and-physical state (hypnagogic transition period or the like) occurs. On the other hand, the time series data of the emphasis displacement inclination in FIG. 22 shows that a hypnagogic omen signal peculiar to a hypnogogic transition period showing a change of twice or more occurs in the vicinity of 700 seconds to 1200 seconds compared with the amplitude before and after the peak zone. From the time series data of the emphasis displacement inclination in FIG. 22, judgment is made such that point 1 shown by a numeral in the drawing is an awakening state, point 2 to point 4 are in a hypnagogic transition period, and point 5 to point 6 are in a sleeping, and comparing them with the observation results by the observer, they show an extremely good agreement.

In FIG. 21, a maximum Lyapnov index which is a chaos index is calculated together and shown as the time series data, and in FIG. 22, the time series data of the maximum Lyapunov index inclination calculated by slide calculation of the maximum Lyapunov index time series data using the same method as the above-described emphasis displacement inclination operating means are shown. As a result, an opposite phase relation between the time series data of the emphasis displacement inclination and the time series data of the maximum Lyapunov index inclination is found in the vicinity from 800 seconds to 1200 seconds, which is confirmed as a hypnagogic transition period.

TEST EXAMPLE 3

(Comparison Between Fingertip Volume Pulse Wave and Living Body Displacement Signal Collected Via Muscles of Buttocks)

A testee was seated on a passenger seat of the car used in Test Example 2, a driving from Miyajima to Iwakuni along the down line of Sanyo Express Way was conducted, and a fingertip volume pulse wave was collected. At the same time, a living body displacement signal including a buttocks pulse wave was collected via the muscles of the buttocks with a pressure sensor. A relation between the time series data of the emphasis displacement inclination and the mental-and-physical state was studied for both fingertip volume pulse wave and living body displacement signal. An observer was seated on the rear seat, and observed the state changes of the testee. The testee was a healthy Japanese male in his age of 20's, 168 cm tall, and 85 Kg. The result is shown in FIGS. 33A and 33B. FIG. 33A is time series data of the emphasis displacement inclination of the fingertip volume pulse wave, and FIG. 33B is the time series data of the emphasis displacement inclination of the living body displacement signal via the muscles of the buttocks.

In the time series data of the emphasis displacement inclination of the fingertip volume pulse wave in FIG. 33A, large amplitude changes appear in the vicinity of 600 to 740 seconds showing a peak in the vicinity of 650 seconds, in the vicinity of 740 to 920 seconds showing a peak in the vicinity of 850 seconds, and in the vicinity of 920 to 1060 seconds showing a peak in the vicinity of 980 seconds, compared with the amplitudes before and after the respective peak zones, which can be judged as a hypnagogic omen signal, and it is judged to reach a sleep in the vicinity of 1120 seconds. When compared with the time series data of the maximum Lyapnov index inclination, an opposite phase relation was clearly observed within the range, so that the above range was confirmed to be a hypnagogic transition period. In order to assure the accuracy of the judgment, it is desirable to use the time series data of the maximum Lyapunov index inclination together, and it is desirable to have a structure to judge that a hypnagogic omen signal is generated at a time passing both peak points (in the vicinities of 650 seconds, 850 seconds, and 980 seconds in FIG. 33A) a little within the range showing the opposite phase relation, and to give a warning. Note that the mental-and-physical state judged from FIG. 33A showed a good agreement with the observation results by the observer.

On the other hand, in the time series data of the emphasis displacement inclination of a living body signal collected via the muscles of the buttocks in FIG. 33B, large amplitude changes appear in the vicinity of 670 to 720 seconds showing a peak in the vicinity of 680 seconds, in the vicinity of 780 to 900 seconds showing a peak in the vicinity of 810 seconds and in the vicinity of 920 to 980 seconds showing a peak in the vicinity of 940 seconds, compared with the amplitudes before and after the respective peak zones, which can be judged as a hypnagogic omen signal, and it is judged to reach a sleep in the vicinity of 1120 seconds. When overlapping the time series data of the maximum Lyapunov index inclination with this, opposite phase relations are confirmed within the above described ranges. It is also desirable to have a structure to judge that a hypnagogic omen signal is generated at a time passing both peak points a little within the range showing the opposite phase relation, and to give a warning. Although the data in FIG. 33B are not always completely consistent with the data in FIG. 33A, it can be judged that they show nearly a similar tendency, and even when a living body displacement signal is collected via the muscles of the buttocks, the mental-and-physical state of a person can be judged with the same accuracy to a fingertip volume pulse wave. In the case of the fingertip volume pulse wave, an optical fingertip pulse wave meter or the like is set in a car and though a hand and fingers are restrained, since in the case of collecting a living body displacement signal via the muscles of the buttocks, no specific restraint is required for the measurement and riding on a car can be performed as usual, it is suitable as a system to judge the mental-and-physical state of a crew of a car or the like, especially that of a driver of a car.

TEST EXAMPLE 4

(Comparison Between Fingertip Volume Pulse Wave and Brain Wave)

A testee was laid on a bed set in a laboratory and a sleeping experiment was carried out. A fingertip volume pulse wave was collected and a relation between the time series data of the emphasis displacement inclination and the mental-and-physical state was studied. At the same time, an electroencephalograph was set on a head and the brain wave was also measured. The testee is a healthy Japanese female in her age of 30's. FIG. 34 shows the time series data of the emphasis displacement inclination for about 30 minutes measured by the present experiment, the time series data of the maximum Lyapunov index inclination, the brain wave waveform measured actually, the analytical waveform of the brain pulse waveform, and the frequency analysis of the analytical waveform.

First, when studied the time series data of the emphasis displacement inclination of the fingertip volume pulse wave, larger amplitude changes are found to appear in the vicinity of 360 and 500 seconds (A zone) showing a peak in the vicinity of 450 seconds, in the vicinity of 500 to 720 seconds showing a peak in the vicinity of 650 seconds (B zone) compared with the amplitude before and after the peak zone. In the vicinities of 450 seconds and 650 seconds, an opposite phase relation appears with the time series data of the maximum Lyapunov index. Therefore, it is possible to judge the vicinity to be a hypnagogic omen signal. Moreover, since the amplitude fluctuation is settled in the vicinity of 860 to 900 seconds, it is possible to judge that a sleeping state appears in this vicinity.

Meanwhile, the measurement using an electroencephalograph found a phenomenon that an alpha rhythm continuously appears in the A zone, and the appearance of the alpha rhythm changes into an intermittent manner in the B zone, and a theta rhythm predominantly occurs in the C zone and the alpha rhythm completely disappears between 860 and 900 seconds, and a beta rhythm appears in the D zone. As a result, it is found that a sleeping state can be judged to have been reached when the alpha rhythm has completely disappeared (between 860 to 900 seconds), which nearly agrees with the judgment by the emphasis displacement inclination of the fingertip volume pulse wave.

Since the alpha rhythm is appeared in the A zone and the B zone, they are defined as an awakening period in an electroencephalograph here. Whereas, a state that a theta rhythm exists predominantly while an alpha rhythm is disappeared is defined as a sleeping state. It is possible to judge a state before appearance of the alpha rhythm becomes intermittent and rapid transition into a hypnagogic state occurs thereafter, namely from a latter half of the B zone to a first half of the C zone, to be a hypnagogic omen period by the electroencephalograph. However, if a warning is emitted at the time, it is too late for the driver or the like of a car as a warning timing. In other words, since a state where an alpha rhythm appears intermittently is already an absent-minded state, and it rapidly goes into a hypnagogic state, there is no time to spare for preventing a traffic accident before it happens.

On the contrary, when judging from the time series data of the emphasis displacement inclination of the fingertip volume pulse wave in FIG. 34, a hypnagogic omen signal (in the vicinity of 450 seconds) showing a displacement amplitude which is clearly different from the time series in front and behind thereof can be detected in the A zone to be judged as an awakening period during which the alpha rhythm appears continuously by the electroencephalograph. Thus, it is understood that it can detect a hypnagogic omen earlier than the electroencephalograph. Accordingly, a method of judgment of the mental-and-physical state by the emphasis displacement inclination of a living body displacement signal is especially effective as a warning system to a driver.

TEST EXAMPLE 5

(Judgment Test of Person and Thing)

Under conditions similar to the test in a dynamic state in Test Example 1, in other words, the seat 100 shown in FIG. 1 was set on a vibrator and was vibrated with a random vibration collected in Michigan in US, and the pressure fluctuation was collected using a pressure sensor as signal data for the cases when a person was seated and when a baggage was put on a seat cushion 120. The testee was a Japanese female weighing 47 Kg, and a 40 Kg weight was used as the baggage. The result is shown in FIG. 23 and FIG. 24.

Figure 23:
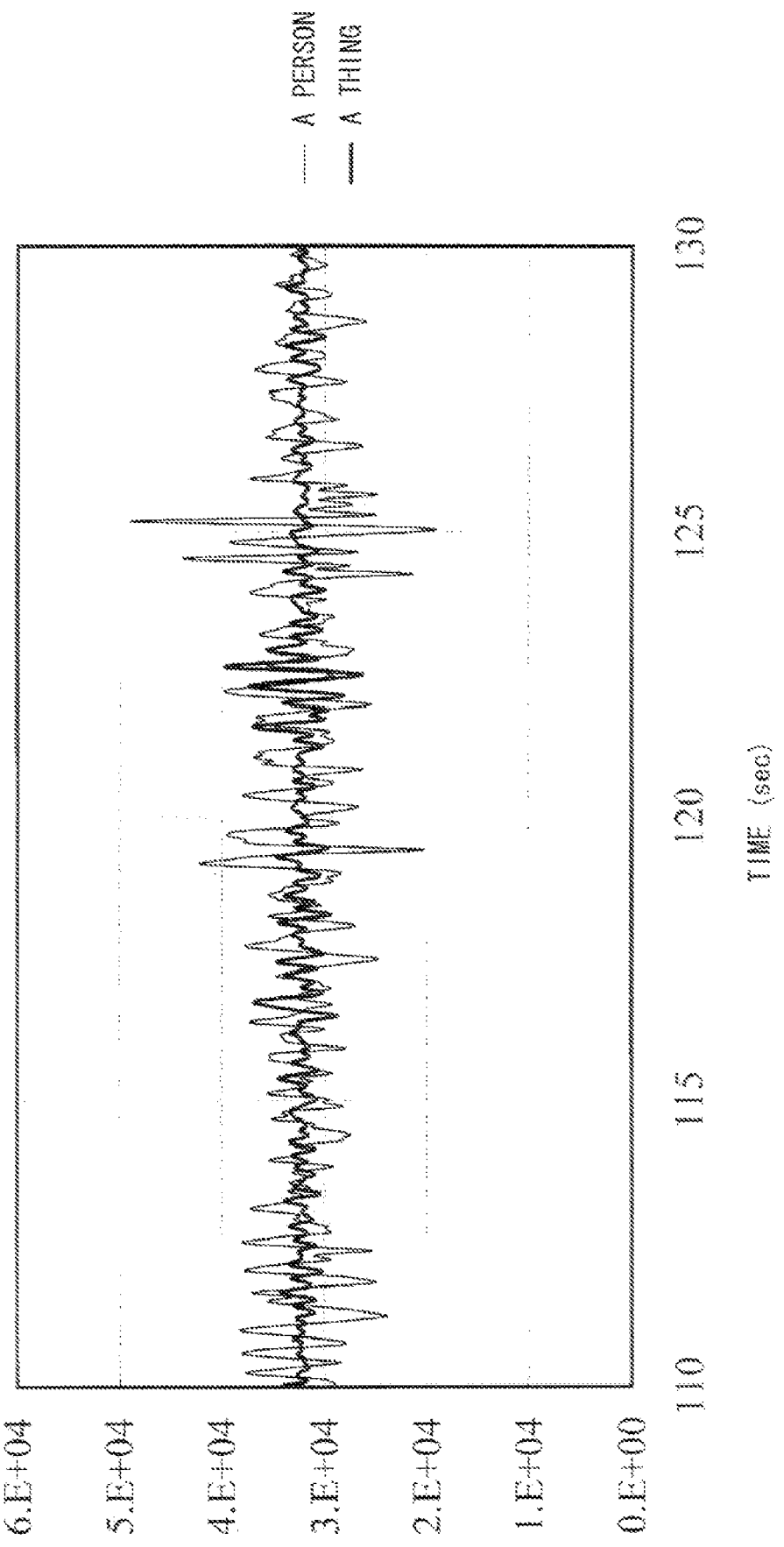
FIG. 23 is a view showing an original waveform obtained from the pressure sensor in a judgment test of a person and a thing in test example 5.

As shown in FIG. 23, pressure fluctuation signals by the random vibration are mixed in the original waveform obtained from the pressure sensor as noise signals. Accordingly, the original waveforms, both in the case of a person and in the case of a thing (baggage), fluctuate randomly, it is impossible to specify whether or not a living signal is contained in an obtained signal. In other words, it is impossible to establish a threshold value to clearly distinguish between a person and a thing.

Figure 24:
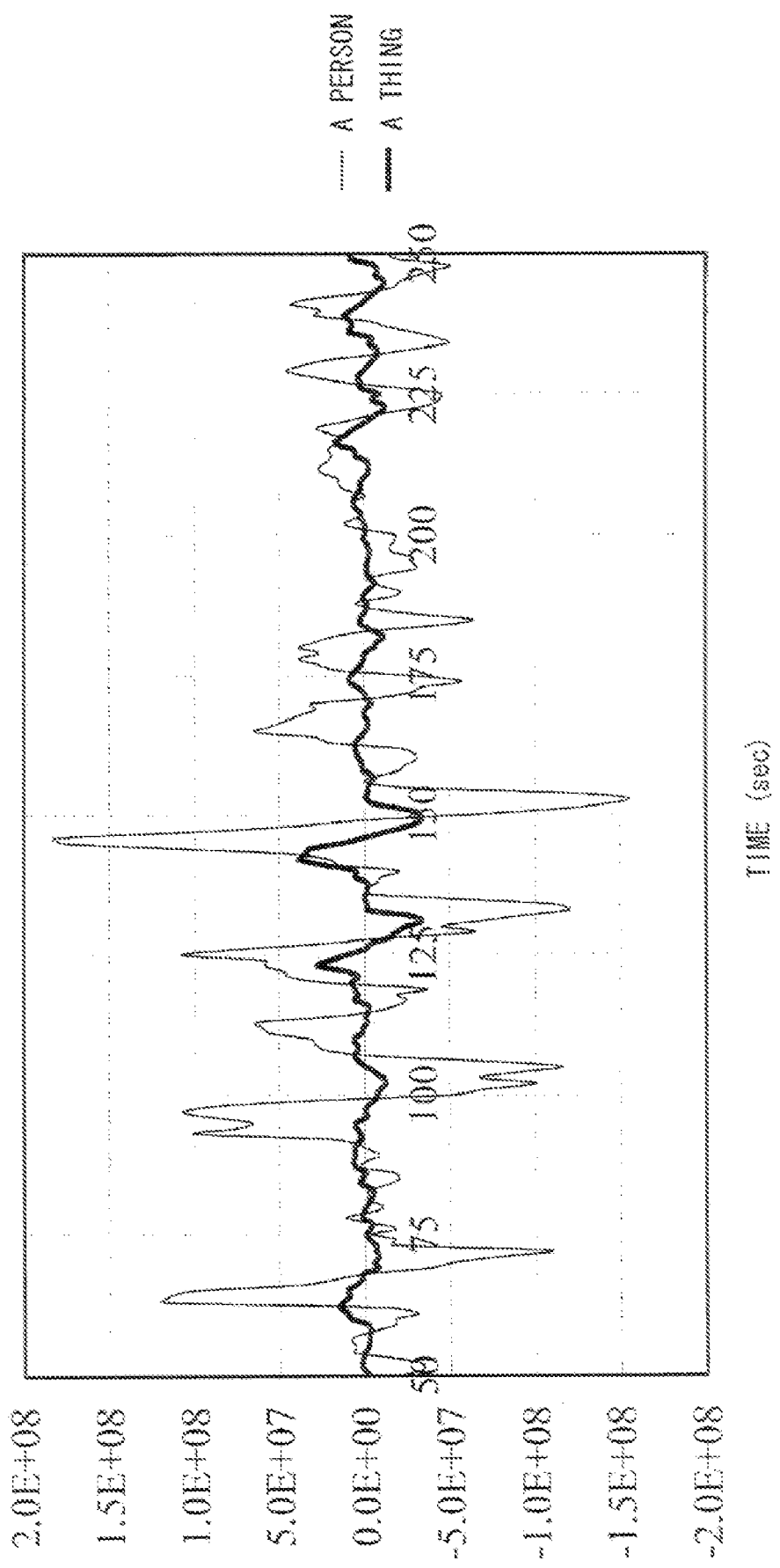
FIG. 24 is a view showing a time series change of an emphasis displacement inclination obtained by operating the original waveform in FIG. 23 at an operating unit.

On the other hand, FIG. 24 shows the time series change of the emphasis displacement inclination obtained by operating the original waveform in FIG. 23 by the operating unit 20. In the case of a thing (baggage), the time series change shows no large fluctuation in FIG. 24, and settles within a prescribed fluctuation range. Whereas, in the case of a person, it clearly has a larger fluctuation range compared with the time series change of a thing. In other words, it is possible to judge it to be a thing when the time series change of the emphasis displacement inclination settles within a prescribed range, and to be a person when exceeding the prescribed range. Accordingly, when a threshold value is established at a prescribed width with no zero inclination as a center, it is possible to draw a distinction between a person and a thing precisely. Since a value (threshold value) in a prescribed range to distinguish between a person and a thing differs according to a type and performance of a sensor used, it is hard to determine the value unconditionally. However, it is possible in general to determine the average value of the time series change of an emphasis displacement inclination to be in the range of one half or less for the case of a person, more preferably one third or less.

Then, when a load body on a seat is thus determined to be a person or a thing, the signal is outputted to a operation control unit of an air bag or the like via the output means 24 as described above, and a prescribed control is performed.

It should be noted that the present invention is not limited to the above-described embodiment. Although in the above-described embodiment, the mental-and-physical state of a person or distinction between a person and a thing is judged from the time series change of the emphasis displacement inclination in the state judging means 23, the time series change of the emphasis displacement inclination, be it in a dynamic state or in a static state, has a characteristic to some extent for each individual as shown in FIG. 15. Moreover, when conducting a frequency analysis as shown in FIG. 16, the dynamic state and the static state are nearly coincident, and by considering not only the time series change of the emphasis displacement inclination but also together with the frequency analysis, if a reference pattern of a certain individual is stored in a storage unit of a computer, it is possible to perform identification of an individual as for whether the time series change of newly detected emphasis displacement inclination and the frequency analysis result are closely analogous to the reference pattern by activating the comparison means (comparison step) 23c as a program established in the state judging means 23 (refer to FIGS. 31A, 31B and 31C). Using this structure, for instance, by detecting a living body signal when a person is seated on the driver's seat, and by determining whether or not the result obtained by conducting calculation of the emphasis displacement inclination and the frequency analysis is coincident with the reference pattern, it is possible to apply this embodiment as an antitheft system of a car if a control circuit is provided enabling the engine to start only when the above-described result is coincident with the reference pattern. (refer to FIGS. 31A, 31B and 31C).

Furthermore, by taking a structure enabling to transmit the living body signal information obtained by the load body state judging device 1 to an external receiver (not shown) from the output means 24, in the case of, for instance, a big traffic accident difficult for emergency crews to approach near, and when the load body state judging device 1 of the present invention is working, it is possible to obtain survival information for the passengers in a car by providing an external receiver on the emergency crews side. Accordingly, it is possible to expect a more efficient first aid activities compared with the case of conducting first aid activities without the benefit of such survival information. Moreover, as described above, by taking a structure possible to transmit the living body signal information to the outside from the output means 24, it becomes possible to detect abnormal states such as the cessation of the heartbeat, respiratory arrest, or the like with an external receiver, at the time of normal traveling so that more prompt first aid can be expected even in such a case.

Figure 25:
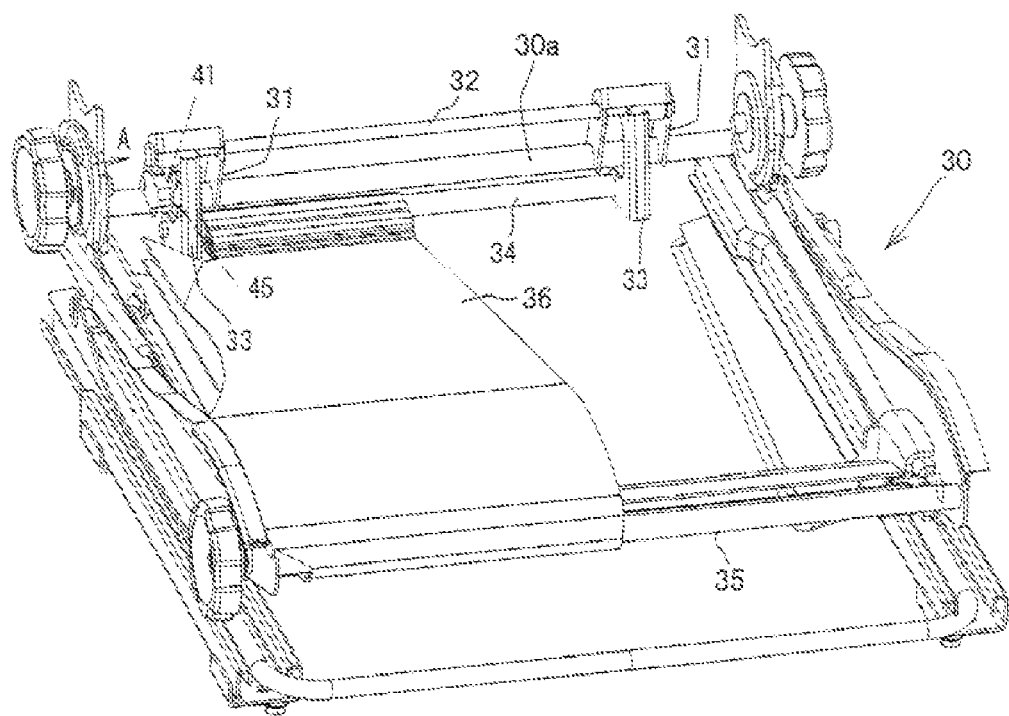
FIG. 25 is a view showing a structural example of a seat cushion of a seat to which a displacement detection mechanism is attached.

Further, the load body state judging device 1 of the present invention can take a structure provided with a load detecting means to detect the load of a load body. For instance, the seat cushion 30 is structured as shown in FIG. 25 so that the structure is provided with a displacement detecting mechanism which is a load detecting means. The seat cushion 30 in FIG. 25 is provided with two brackets 31 and 31 to a rear frame 30a placed at the back in the lateral direction (width direction), a torsion bar 32 is supported by the brackets 31 and 31, two arms 33 and 33 are connected to the torsion bar 32, a supporting frame 34 is disposed to the arms 33 and 33, and a base cushioning material 36 made of a solid knitted fabric or the like is strained between the supporting frame 34 and a front end frame 35. Then, when a person or a thing is put on a surface layer cushioning material (not shown), the arms 33, 33 and the supporting frame 34 pivots in front and behind due to an elastic force of the torsion bar 32 and performs displacement. Therefore, by detecting the displacement of the arm 33, it is possible to detect the load.

Figure 26:
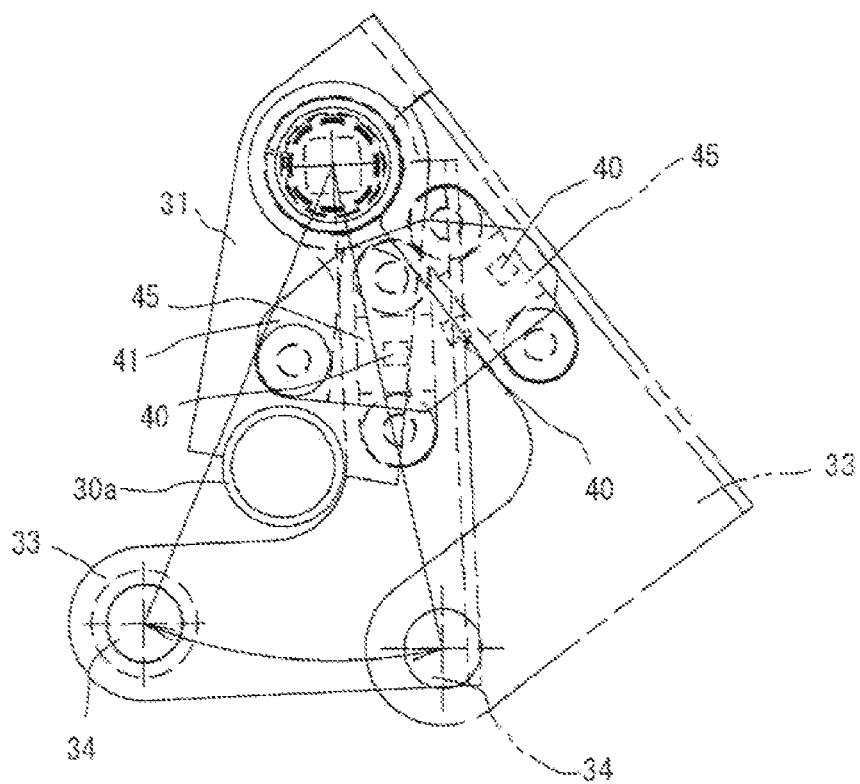
FIG. 26 is an A-arrow diagram of FIG. 25.
Figure 27:
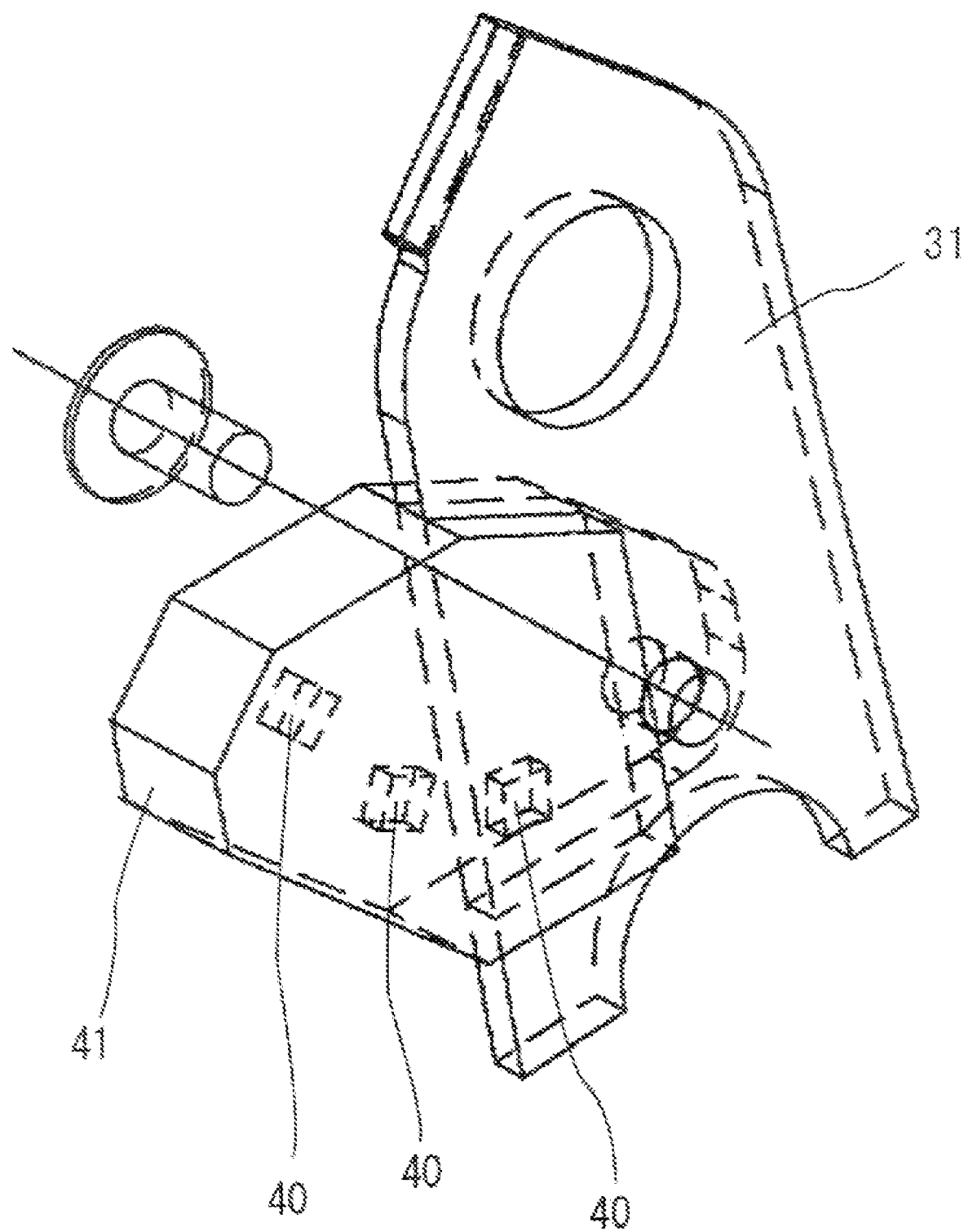
FIG. 27 is a view showing the details of a hole IC fixing bracket.

A combination of holes IC 40 and a magnet 45 as a magnetic sensor is used as a displacement detecting mechanism in FIG. 24 to FIG. 27. Three pieces of the holes IC 40 are arranged to a hole IC fixing bracket 41 at almost the same intervals in nearly an arc shape as shown in FIG. 26 and FIG. 27, and the hole IC fixing bracket 41 is fixed on a side surface of the bracket 31 fixed to the rear frame 30a. Whereas, the magnets 45 are fixed on side surfaces of the arms 33 so as to face the hole IC fixing brackets 41. The arms 33 pivot in the direction to tilt forward when the base cushioning material 36 is depressed by a person being seated. Accordingly, when the amount of the pivoting is changed, respective output voltages of three hole ICs 40 arranged in nearly an arc shape on which the magnetic field caused by the magnets 45 works, changes according to the change of the magnetic flux density. Making good use of this relation, a correlation between fluctuation of the output voltage of each hole IC 40 and the pivot angle of the arm 45, and a correlation between the pivot angle and the load are defined. Then, by establishing these correlations on a microcomputer or the like similarly to the above-described embodiment, it is possible to detect the load of a seated person or a thing on the seat cushion 30.

In FIG. 26 and FIG. 27, the hole IC fixing bracket 41 is provided on a side surface of the bracket 31, and the magnets 45 are also disposed on the side surfaces of the arms 33. When arranging in this manner, the opposing portions of the hole IC fixing bracket 41 to the magnets 45 shift accompanying the pivoting movement of the arms 33. If such a shift occurs, if only one pieces of the hole IC bracket 40 is provided, since the hole IC 40 is high in directivity, it is sometimes difficult to detect a magnetic field. Accordingly, when the magnet 45 is fixed on the side surface of the arm 33, it is preferable to provide a plurality of hole ICs 40 in nearly arc shape to the hole IC bracket 41 fixed to a side surface of the bracket 31, corresponding to a pivoting range of the arm 33 (magnet 45). Further, when a structure to amplify the pivoting angle of the arm 33 by disposing a gear mechanism (not shown) such as a worm wheel which rotates with displacement of the arm 33 and by attaching the magnet 45 or the like at an arbitrary position on the gear mechanism, or the like, it is desirable because the detection accuracy of a load can be increased.

Figure 28:
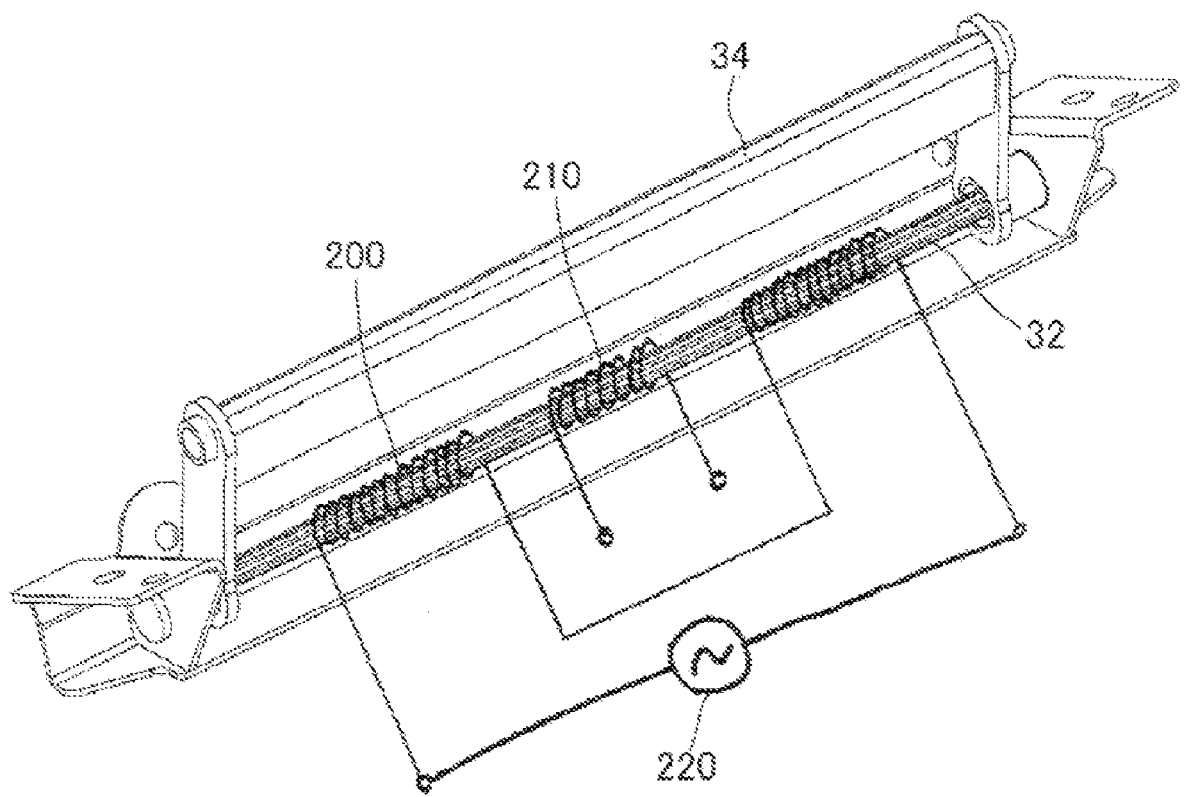
FIG. 28 is a view showing an example of a displacement detecting mechanism provided with an exciting coil and a pick up coil to a torsion bar.
Figure 30:
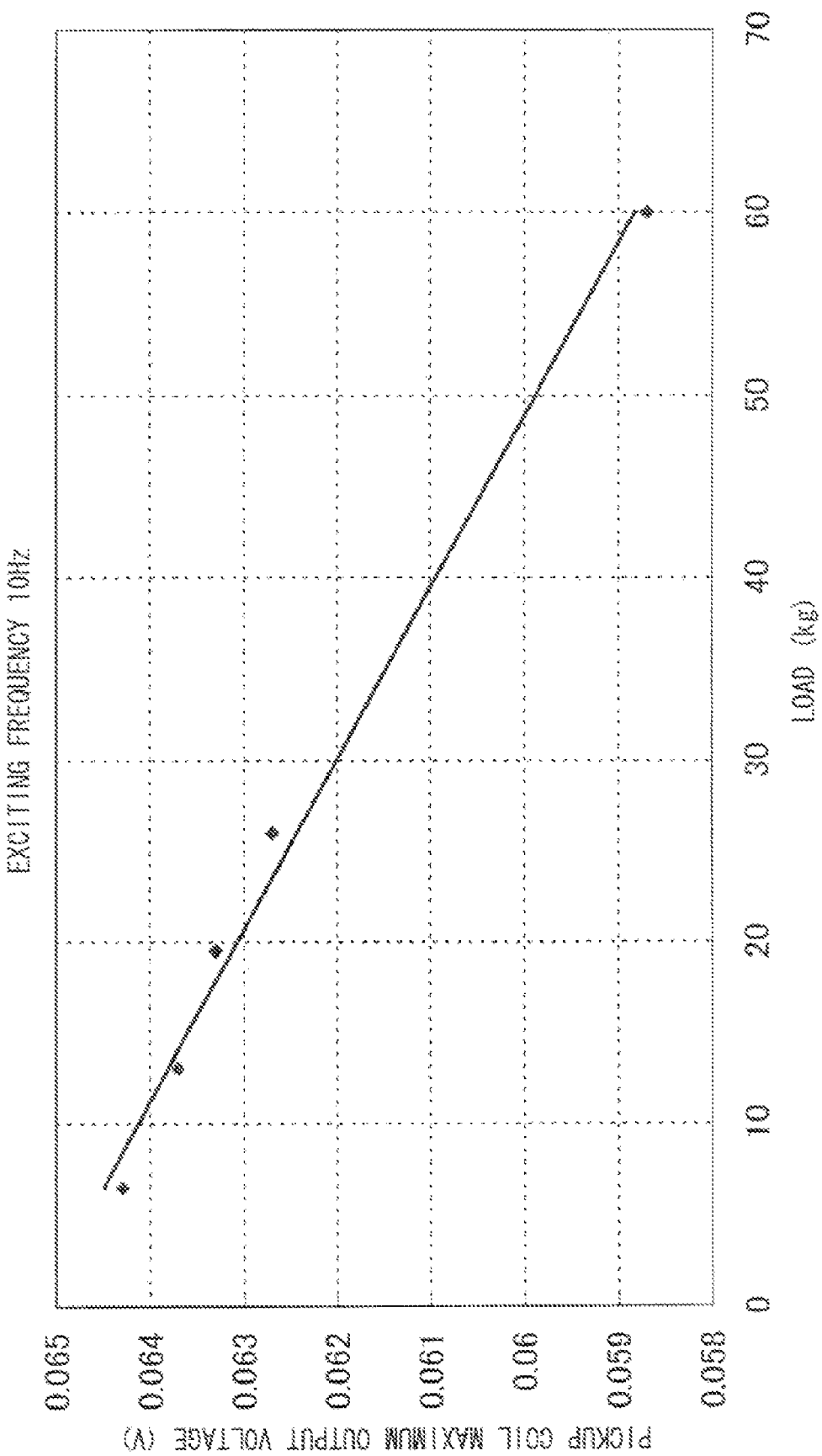
FIG. 30 is a graph showing a relation between a load and an output voltage of the pick up coil.
Figure 31A:
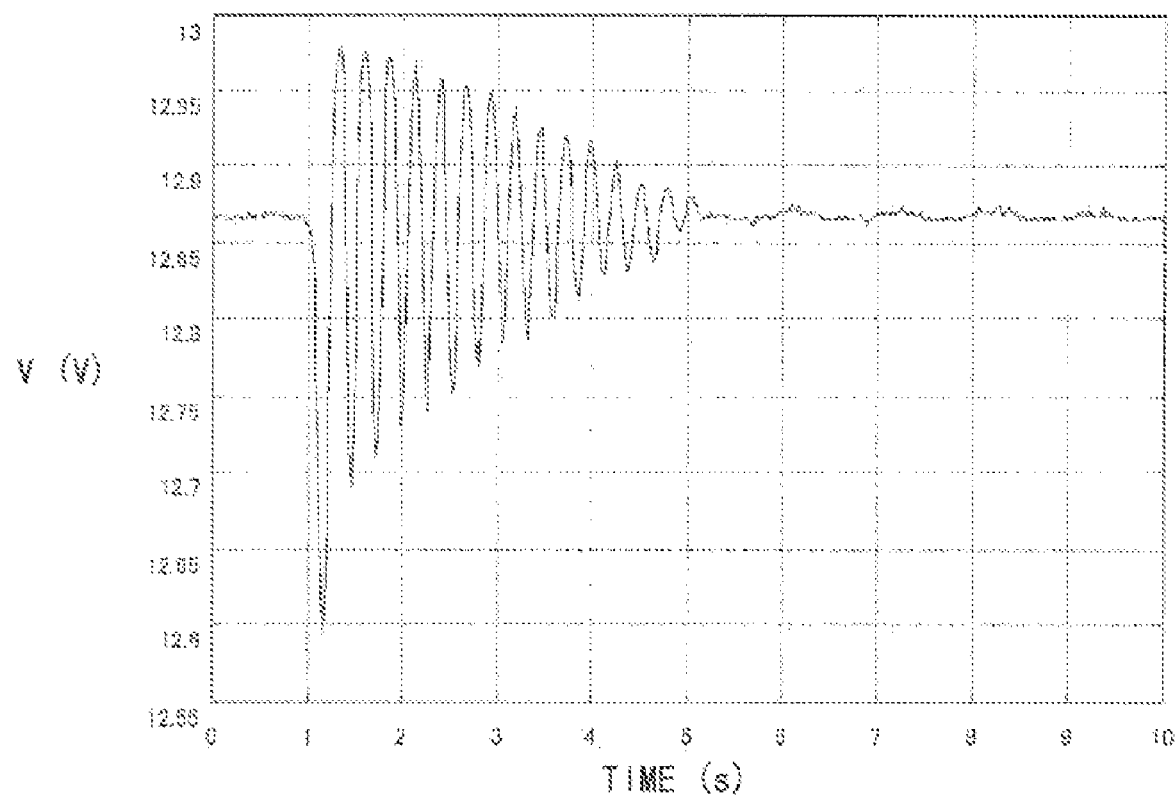
FIG. 31A is a graph showing a relation between the magnitude of the vibration and the output voltage.
Figure 31B:
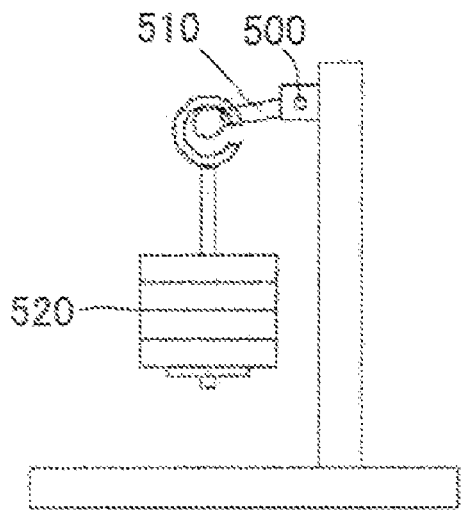
FIGS. 31B and 31C are views to explain a measurement method.
Figure 31C:
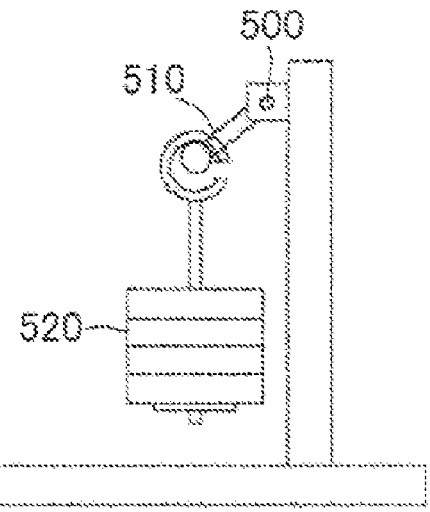
Figure 32:
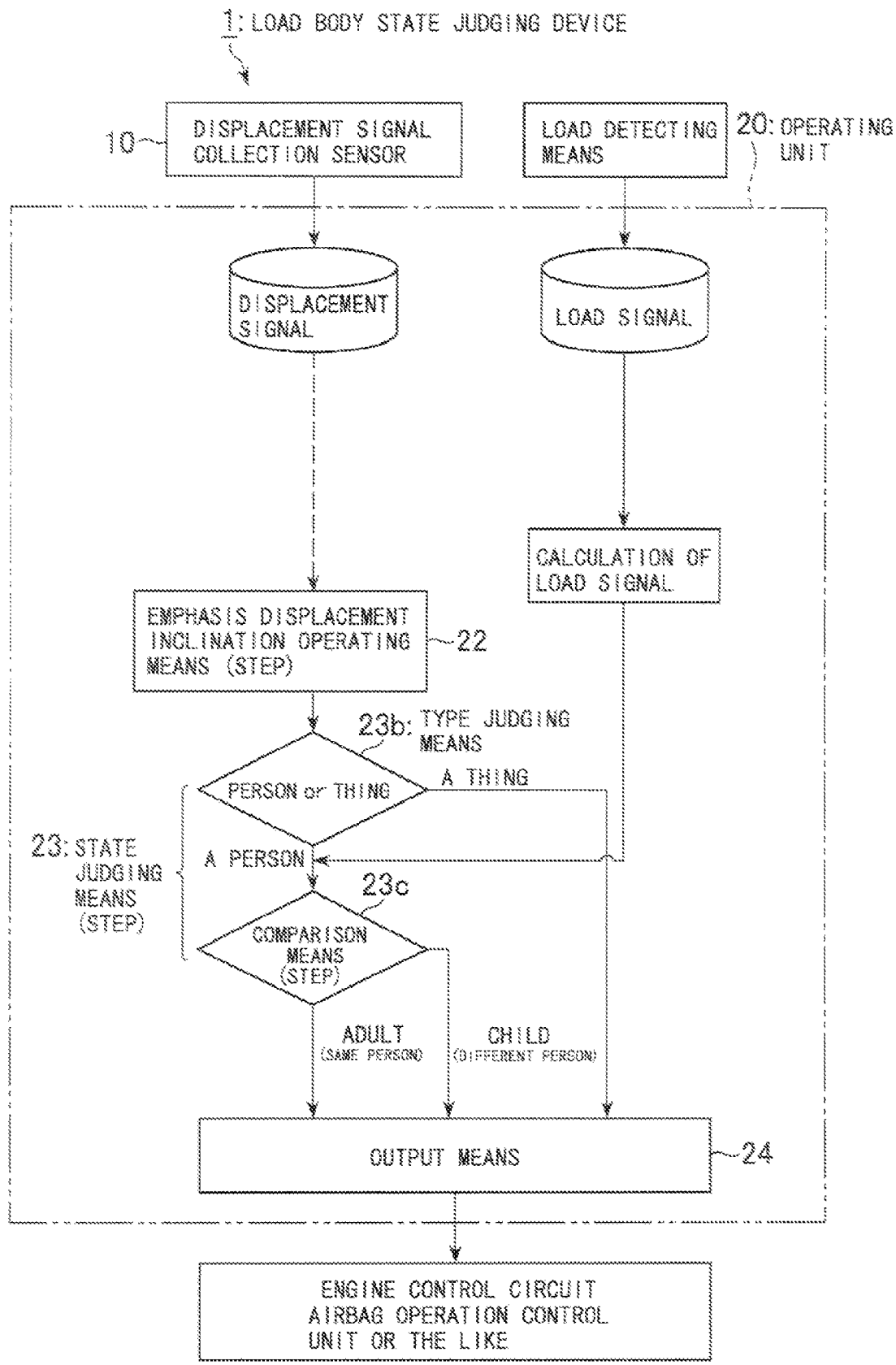
FIG. 32 is a block diagram showing a schematic structure of the load body state judging device when using a load signal obtained from a load detection means.

Moreover, as a displacement detection mechanism, it is possible to use a strain gauge (not shown) which is attached to the torsion bar 32 and directly measures the strain of the torsion bar 32, other than this. Furthermore, as shown in FIG. 28, an exciting coil 200 and a pickup coil (secondary coil) 210 are wound around the torsion bar 32, and induced current if fed to the exciting coil 200 using an alternating current power supply 220. Then, it is possible to use a displacement detecting mechanism to measure an inducting voltage obtained from the pick up coil 210. Since the stress generated in the torsion bar 32 varies according to the load of the load body, the inducting voltage varies. FIG. 30 is a graph showing the correlation between a static load and an output voltage of the pick up coil, and as shown in the drawing, when the load increases the magnetic resistance increases while the output voltage decreases. FIG. 31A shows a graph showing a relation between the magnitude of vibration and the output voltage. This is an investigation of voltage fluctuation generated when a weight 520 of 40 Kg is hung on ar arm 510 connected to a torsion bar 500 as shown in FIG. 31B, and pushed downward by 10 mm and released as shown in FIG. 31C. The measurement was carried out such that an exciting coil and a pick up coil were wound on the torsion bar 500 (not shown), the exciting frequency was set to be 50 Hz, and the sampling time was set to be 10 μS. As clearly understood from FIG. 31A, the voltage fluctuation becomes small according to progress of the attenuation, which shows the possibility of detecting the vibration change.

Though the arrangement of the exciting coils 200 and the pick up coils provided to the torsion bar 32 is not limited, as for the pick up coil, it is preferable to wind two pieces of pick up coils 210 and 211 separately at one end side and the other end side of the torsion bar. Since the torsion bar 32 is twisted around the one end, there is a difference in stress between one end side and the other end side. This difference in stress makes output voltage fluctuation. In addition to that, the torsion bar 32 is affected by movement caused by the seat structure such as a clearance or the like, when an external input acts Therefore, if only one pick up coil is provided, since it is would around the torsion bar 32, an output voltage is generated by a slight movement of the pick up coil though the stress of the torsion bar 32 is not fluctuated. Whereas, when two pick up coils 210 and 211 are provided, even when output voltage is created due to the pick up coils, since the two coils 210 and 211 move together, the output voltage is cancelled so that the reliability of the detection is enhanced.

When the load detecting means is provided in this manner, the device is structured such that a load signal obtained from the load detecting means is inputted into the operating unit 20. When a load fluctuation is found in time series at the time of judging whether or not a load fluctuation exists by the type judging means 23b at the state judging means (step) 23, it means occurrence of a body movement. Therefore judgment is made to be "a person", and thus the correctness of the judgment is improved.

A load based on the load signal is considered in the comparison means (comparison step) 23c established in the state judging means 23, and it is compared with a reference load stored in advance in the storage unit, which makes it possible to distinguish between big and small in terms of physique, to distinguish an adult from a child, or to identify an individual. It is especially effective when distinguishing between an adult and a child. When conducting identification of an individual (distinction between one and the same person or a different person), since it is possible to judge whether or not the individual is consistent with a reference load registered in advance or a reference value for a living body certification by consideration of the load or wobbling fluctuation of the load, which will be described later, in addition to a time series change of the emphasis displacement inclination, it is possible to identify an individual more precisely.

Supposing that a dynamic load fluctuation caused by body movement can be detected using a load detecting means such as a displacement detection mechanism using the above-described exciting coil is taken as time series data, it is possible to show the wobbling fluctuation of a living body caused by a body movement, which is one of the living body displacement signals. Accordingly, it is also possible to use the load detecting means as a displacement signal collection sensor of the present invention instead of a pressure sensor, not to provide it as a carrier of a different function from the pressure sensor.

It should be noted that although a vehicle seat used for a transportation device such as a car, a train, or a plane is named as a load body supporting means in the above explanation, the present invention is also applicable to an office-use seat, a seat to be seated by a person at the time of physical checkup, a diagnosis or the like in a hospital or the like, or to bedclothes such as bedding, mattress, a bed or the like. However, it is most suitable for a vehicle seat because it can reduce the effect of noises and precisely judge a mental-and-physical state or distinction between a person and a thing.

The invention claimed is:

1. A load body state judging device to judge a state of a load body by analyzing signal data obtained by a displacement signal collection sensor which can collect a living body displacement signal of the load body supported by a load body supporting means, comprising:

an average displacement inclination operating means to divide an original waveform of signal data obtained through said displacement signal collection sensor into each prescribed time range and determine a rate of change of the signal data in the prescribed time range as an average displacement inclination;

an emphasis displacement inclination operating means to determine an emphasis displacement inclination by slide-calculating a rate of change of an average displacement inclination for each prescribed sampling time at a prescribed slide lap rate over prescribed number of times from time series data of said average displacement inclination so that the time series data of the emphasis displacement inclination is obtained; and a state judging means to judge a load body state from the time series data of the emphasis displacement inclination obtained by said emphasis displacement inclination operating means;

wherein said displacement signal collection sensor is attached to the load body supporting means;

wherein said average displacement inclination operating means comprises:

an original waveform displacement inclination operating means to divide an original waveform of signal data obtained by said displacement signal collection sensor into each prescribed time range, and further divide it within the prescribed time range into a plurality of intervals, and obtain a rate of change for each interval as an original waveform displacement inclination; and an original waveform displacement inclination summing means to sum up each original waveform displacement inclination obtained by said original waveform displacement inclination operating means, wherein the sum up value obtained by said original waveform displacement inclination summing means is structured to be established as an average displacement inclination;

wherein said state judging means comprises a type judging means to judge the type of the load body; and wherein said type judging means comprises a means to judge a load body to be a thing when the time series data of said emphasis displacement inclination are in transition within a prescribed range, and to be a person when in transition with an inclination change exceeding the prescribed range.

2. The load body state judging device according to claim 1, wherein said original waveform displacement inclination operating means is structured to obtain the rate of change for each interval as said original waveform displacement inclination, taking the distance between respective intersecting points of an envelope on the upper limit side of the amplitude of an original waveform, an envelope on the lower limit side, or a curved line nearly parallel to either envelope, and the original waveform as an interval.

3. The load body state judging device according to claim 1, wherein a sampling time interval used for slide-calculation of said emphasis displacement inclination operating means is 180 seconds, and a slide lap rate is 90%.

4. The load body state judging device according to claim 1, wherein said state judging means further comprises a hypnagogic transition judging means to judge the hypnagogic transition when the load body is a person.

5. The load body state judging device according to claim 4, wherein said hypnagogic transition judging means judges when the amplitude range of time series data of said emphasis displacement inclination gets relatively large compared with the amplitude before or after the range as a hypnagogic transition period between an awakening state and a sleeping state.

6. The load body state judging device according to claim 1, wherein said type judging means comprises a comparison means to read and compare a reference pattern of time series data of the emphasis displacement inclination stored in a storage unit in advance and specify an individual when the time series data of said emphasis displacement inclination are in transition with an inclination change exceeding a prescribed range.

7. The load body state judging device according to claim 6, further comprising a load detection means detecting the load of the load body separately from said displacement signal collection sensor, wherein said comparison means compares the load of the load body obtained by said load detection means with a reference load stored in a storage unit in advance to judge at least any one factor out of physique size, distinction between an adult and a child, and identification of an individual while adding the load to the comparison factors as one factor.

8. The load body state judging device according to claim 1, wherein said load body supporting means is a vehicle seat, and said displacement signal collection sensor is structured to be attached to at least any one portion out of a seat cushion, a seat back, or a headrest, and to detect pressure fluctuation based on a living body displacement signal of the load body.

9. The load body state judging device according to claim 8, wherein said load body supporting means is a vehicle seat, and said displacement signal collection sensor is structured to be attached to at least any one portion of a seat cushion of the vehicle seat, and to detect pressure fluctuation based on a living body displacement signal via the muscles of the buttocks of the load body.

10. The load body state judging device according to claim 1, wherein said load body supporting means is a vehicle seat, and said displacement signal collection sensor is structured to detect a displacement amount of a member displacing based on a living body displacement signal of the load body.

11. The load body state judging device according to claim 1, further comprising a load detection means detecting the load of the load body separately from said displacement signal collection sensor.

12. The load body state judging device according to claims 11 or 7, wherein said load detection means is a displacement detection mechanism to detect a displacement amount of a member displacing based on the load of a load body among the load body supporting means.

13. A vehicle seat, comprising:
a displacement signal collection sensor provided at least any one portion of a seat cushion, a seat back, and a headrest which are load body supporting units, and is able to collect displacement of the load body supporting unit due to a living body signal of the load body supported by said load body supporting unit; and a load body state judging device to analyze signal data obtained from said displacement signal collection sensor and judge the state of the load body, wherein said load body state judging device comprises:
an average displacement inclination operating means to divide an original waveform of signal data obtained through said displacement signal collection sensor into each prescribed time range and to determine a rate of change of the signal data in the prescribed time range as an average displacement inclination;

an emphasis displacement inclination operating means to obtain a rate of change of an average displacement inclination for each prescribed sampling time period from time series data of said average displacement inclination by slide calculating at a prescribed slide lap rate over prescribed number of times as the emphasis displacement inclination so as to obtain time series data of the emphasis displacement inclination; and a state judging means judging a load body state from time series data of the emphasis displacement inclination obtained by said emphasis displacement inclination operating means;

wherein said average displacement inclination operating means of said load body state judging device comprises:
an original waveform displacement inclination operating means to divide an original waveform of signal data obtained by said displacement signal collection sensor into each prescribed time range, and further divide it within the prescribed time range into a plurality of intervals, and obtain a rate of change for each interval as an original waveform displacement inclination; and an original waveform displacement inclination summing means to sum up each original waveform displacement inclination obtained by said original waveform displacement inclination operating means, wherein the sum up value obtained by said original waveform displacement inclination summing means is structured to be established as an average displacement inclination;

wherein said state judging means comprises a type judging means to judge the type of the load body; and wherein said type judging means comprises a means to judge a load body to be a thing when the time series data of said emphasis displacement inclination are in transition within a prescribed range, and to be a person when in transition with an inclination change exceeding the prescribed range.

14. The vehicle seat according to claim 13, wherein said load body supporting unit comprises:

a vibration-removal mechanism having a small spring constant in an equilibrium state; and a cushion mechanism arranged to provide with a spring characteristic closely analogous to the spring characteristics of a human muscle, wherein said displacement signal collection sensor is disposed between said vibration-removal mechanism and the cushioning mechanism.

15. The vehicle seat according to claim 14, wherein said displacement signal collection sensor is disposed between a base cushioning material disposed in a seat cushion and included in said vibration-removal mechanism and a surface layer cushioning material strained on a cushion frame disposed in a seat cushion and included in said cushioning mechanism, and is able to collect a living body displacement signal via the muscles of the buttocks.

16. The vehicle seat according to claim 13, wherein the original waveform displacement inclination operating means of said load body state judging device is structured to obtain the rate of change for each interval as said original waveform displacement inclination, taking the distance between respective intersecting points of an envelope on the upper limit side of the amplitude of an original waveform, an envelope on the lower limit side, or a curved line nearly parallel to either envelope, and the original waveform as an interval.

17. The vehicle seat according to claim 13, wherein a sampling time interval used for slide-calculation of said emphasis displacement inclination operating means included in the load body state judging device is 180 seconds, and a slide lap rate is 90%.

18. The vehicle seat according to claim 13, wherein the state judging means of said load body state judging device further comprises a hypnagogic transition judging means to judge the hypnagogic transition when the load body is a person.

19. The vehicle seat according to claim 18, wherein said hypnagogic transition judging means judges when the amplitude range of time series data of said emphasis displacement inclination gets relatively large compared with the amplitude before or after the range as a hypnagogic transition period between an awakening state and a sleeping state.

20. The vehicle seat according to claim 18, further comprising a load detection means detecting the load of a load body, wherein the comparison means compares the load of the load body obtained by the load detection means with a reference load stored in a storage unit in advance to judge at least any one factor out of physique size, distinction between an adult and a child, and identification of an individual while adding the load to the comparison factors as one factor.

21. The vehicle seat according to claim 13, further comprising a load detection means detecting the load of a load.

22. A computer readable medium having a computer program to judge load body state by analyzing with a microprocessor signal data obtained from a displacement signal collection sensor which is able to collect a living body displacement signal of the load body supported by the load body supporting means, said computer program comprises:

an average displacement inclination operating step to divide an original waveform of signal data obtained through said displacement signal collection sensor into each prescribed time range and determine a rate of change of the signal data in the prescribed time range as an average displacement inclination;

an emphasis displacement inclination operating step to determine an emphasis displacement inclination for each prescribed sampling time at a prescribed slide lap rate over a prescribed number of times from time series data of the average displacement inclination so that the time series data of the emphasis displacement inclination is obtained; and a state judging step to judge a load body state from the time series data of the emphasis displacement inclination obtained by said emphasis displacement inclination operating step;

wherein said average displacement inclination operating steps comprises:

an original waveform displacement inclination operating step to divide an original waveform of signal data obtained by said displacement signal collection sensor into each prescribed time range, and further divide it within the prescribed time range into a plurality of intervals, and obtain a rate of change for each interval as an original waveform displacement inclination; and an original waveform displacement inclination summing step to sum up each original waveform displacement inclination obtained by said original waveform displacement inclination operating step, wherein the sum up value obtained by said original waveform displacement inclination summing step is structured to be establish as an average displacement inclination;

wherein said state judging step comprises a type judging step to judge the type of the load body; and wherein said type judging step comprises a step to judge a load body to be a thing when the time series data of said emphasis displacement inclination are in transition within a prescribed range, and to be a person when in transition with an inclination change exceeding the prescribed range.

23. The computer readable medium according to claim 22, wherein said original waveform displacement inclination operating step is structured to obtain the rate of change for each interval as said original waveform displacement inclination, taking the distance between respective intersecting points of an envelope on the upper limit side of the amplitude of an original waveform, an envelope on the lower limit side, or a curved line nearly parallel to either envelope, and the original waveform as an interval.

24. The computer readable medium according to claim 22, wherein a sampling time interval used for slide-calculation of said emphasis displacement inclination operating step is 180 seconds, and a slide lap rate is 90%.

25. The computer readable medium according to claim 22, wherein said state judging step further comprises a hypnagogic transition judging step to judge the hypnagogic transition when the load body is a person.

26. The computer readable medium according to claim 25, wherein said hypnagogic transition judging step judges when the amplitude range of the time series data of the emphasis displacement inclination getting relatively large compared with the amplitude before or after the range as in a hypnagogic transition period between an awakening state and a sleeping state.

27. A method of judging load body state by analyzing with a microprocessor signal data obtained from a displacement signal collection sensor which is able to collect a living body displacement signal of the load body supported by the load body supporting means, said method comprising:

providing an original waveform of signal data obtained through said displacement signal collection sensor to a microprocessor;

dividing the original waveform of signal data into each prescribed time range and determining a rate of change of the signal data in the prescribed time range as an average displacement inclination;

determining an emphasis displacement inclination for each prescribed sampling time at a prescribed slide lap rate over a prescribed number of times from time series data of the average displacement inclination so that the time series data of the emphasis displacement inclination is obtained; and judging a load body state from the time series data of the emphasis displacement inclination obtained, wherein an original waveform of signal data obtained is divided by said displacement signal collection sensor into each prescribed time range, and further divided within the prescribed time range into a plurality of intervals, to obtain a rate of change for each interval as an original waveform displacement inclination; and each original waveform displacement inclination obtained is summed up, wherein the sum up value obtained by said original waveform displacement inclination summing step is structured to be establish as an average displacement inclination, wherein said state judging step comprises a type judging step to judge the type of the load body; and wherein said type judging step comprises a step to judge a load body to be a thing when the time series data of said emphasis displacement inclination are in transition within a prescribed range, and to be a person when in transition with an inclination change exceeding the prescribed range.

* * * * *